US009453828B2

(12) United States Patent
Corbett et al.

(10) Patent No.: US 9,453,828 B2
(45) Date of Patent: Sep. 27, 2016

(54) METHOD AND SYSTEM FOR IDENTIFYING AND SAMPLING HYDROCARBONS WITH BUOYS

(71) Applicants: Kevin T. Corbett, Missouri City, TX (US); William E. Bond, Spring, TX (US); Robert J. Pottorf, Houston, TX (US); Aaron B. Regberg, Houston, TX (US); A. Lucie N'Guessan, Houston, TX (US); Scott C. Hornbostel, Houston, TX (US); William P. Meurer, Magnolia, TX (US); Louise Levien, Houston, TX (US); Glenn B. Hieshima, Houston, TX (US); Timothy J. Nedwed, Houston, TX (US)

(72) Inventors: Kevin T. Corbett, Missouri City, TX (US); William E. Bond, Spring, TX (US); Robert J. Pottorf, Houston, TX (US); Aaron B. Regberg, Houston, TX (US); A. Lucie N'Guessan, Houston, TX (US); Scott C. Hornbostel, Houston, TX (US); William P. Meurer, Magnolia, TX (US); Louise Levien, Houston, TX (US); Glenn B. Hieshima, Houston, TX (US); Timothy J. Nedwed, Houston, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 0 days.

(21) Appl. No.: 14/802,754

(22) Filed: Jul. 17, 2015

(65) Prior Publication Data
US 2016/0018377 A1    Jan. 21, 2016

Related U.S. Application Data

(63) Continuation-in-part of application No. 14/752,030, filed on Jun. 26, 2015.

(60) Provisional application No. 62/190,999, filed on Jul. 10, 2015, provisional application No. 62/190,089, filed on Jul. 8, 2015, provisional application No. 62/180,987, filed on Jun. 17, 2015, provisional application No. 62/026,449, filed on Jul. 18, 2014.

(51) Int. Cl.
*G01V 5/00* (2006.01)
*G01N 33/18* (2006.01)
(Continued)

(52) U.S. Cl.
CPC .......... *G01N 33/1886* (2013.01); *B63B 22/24* (2013.01); *B63B 27/30* (2013.01); *B63B 2022/006* (2013.01); *Y10S 901/01* (2013.01)

(58) Field of Classification Search
CPC ............ G01N 21/64; G01N 21/6486; G01N 2201/0218
See application file for complete search history.

(56) References Cited

U.S. PATENT DOCUMENTS 7,704,746 B1  4/2010 White et al.
8,492,153 B2  7/2013 Jones et al.
(Continued)

FOREIGN PATENT DOCUMENTS

EP    0678758    10/1995
EP    2113796    11/2009
(Continued)

OTHER PUBLICATIONS

Aeschbach-Hertig, W., et al., (2000), "Palaeotemperature Reconstruction From Noble Gases In Ground Water Taking Into Account Equillibration With Entrapped Air", Nature, vol. 405, pp. 1040-1044.
(Continued)

*Primary Examiner* — Kiho Kim
(74) *Attorney, Agent, or Firm* — ExxonMobil Upstream Research Company, Law Department

(57) ABSTRACT

Method and system is described for hydrocarbon exploration and development. The method and system include one or more remote devices, such as buoys, which are utilized to identify and collect samples of target materials. The buoys include measurement components, sampling components and storage components to manage the obtained samples.

32 Claims, 9 Drawing Sheets

(51) Int. Cl.
  *B63B 22/24* (2006.01)
  *B63B 27/30* (2006.01)
  *B63B 22/00* (2006.01)

(56) References Cited

U.S. PATENT DOCUMENTS

| | | | |
|---|---|---|---|
| 8,599,382 | B2 | 12/2013 | Pierce, Jr. et al. |
| 8,883,417 | B2 | 11/2014 | Jacobs et al. |
| 9,146,225 | B2 | 9/2015 | Pottorf et al. |
| 2003/0170909 | A1 | 9/2003 | Schaumloffel |
| 2004/0037747 | A1 | 2/2004 | Sternberger et al. |
| 2007/0078610 | A1* | 4/2007 | Adams ............... G01N 1/10 702/28 |
| 2010/0042324 | A1 | 2/2010 | Murphy |
| 2011/0009019 | A1* | 1/2011 | Neira ............... G01N 1/14 441/1 |
| 2011/0308790 | A1 | 12/2011 | Strapoc et al. |
| 2012/0165215 | A1 | 6/2012 | Andersen et al. |
| 2013/0037707 | A1 | 2/2013 | Lamberti et al. |
| 2013/0116126 | A1 | 5/2013 | Ashby et al. |
| 2014/0152455 | A1 | 6/2014 | Giori et al. |
| 2014/0191893 | A1 | 7/2014 | Fox et al. |
| 2014/0378319 | A1 | 12/2014 | Regberg et al. |
| 2015/0007648 | A1 | 1/2015 | Theron et al. |
| 2015/0038348 | A1 | 2/2015 | Ashby et al. |
| 2015/0224502 | A1 | 8/2015 | Pargett et al. |

FOREIGN PATENT DOCUMENTS

| | | | |
|---|---|---|---|
| EP | 2 273 251 | | 1/2011 |
| EP | 2 584 355 | | 4/2013 |
| GB | 2478511 | | 9/2011 |
| KR | 2005045180 | A * | 5/2005 |
| KR | 101313546 | B1 * | 10/2013 |
| WO | 2004/025261 | | 3/2004 |
| WO | 2007/008932 | | 1/2007 |
| WO | WO 2013/071185 | | 5/2013 |
| WO | 2013/148442 | | 10/2013 |

OTHER PUBLICATIONS

Ballentine, C.J., et al., (2002), "Production, Release and Transport of Noble Gases In The Continental Crust", GeoScienceWorld, pp. 481-538.
Ballentine, C.J., et al., (1991), "Rare Gas Constraints On Hydrocarbon Accumulation, Crustial Degassing and Groundwater Flow In The Pannonian Basin", Earth and Planetary Science Letters, vol. 105, pp. 229-246.
Ballentine, C.J., et al., (1996), "A Magnus Opus: Helium, Neon, and Argon Isotopes In A North Sea Oilfield", Geochimica et Cosmochimica Acta, vol. 60, No. 5., pp. 831-849.
Ballentine, C.J., et al., (2002), "Tracing Fluid Origin, Transport and Interaction In The Crust", GeoScienceWorld, pp. 539-614.
Battani, A., et al., (2010), "Trinidad Mud Volcanoes: The Origin of The Gas", AAPG Memoir 93, pp. 225-238.
Bell, R.J., et al., (2007), "Calibration of An In Situ Membrane Inlet Mass Spectrometer For Measurements of Dissolved Gases and Volatile Organics In Seawater", Environ. Sci. Technol., vol. 41, pp. 8123-8126.
Bosch, A., et al., (1988), "Natural Gas Association With Water and Oil As Depicted By Atmospheric Noble Gases: Case Studies From The Southeastern Mediterranean Costal Plan", Earth and Planetary Science Letters, vol. 87, pp. 338-346.
Camilli, R., et al., (2009), "Characterizing Spatial and Temporal Variability of Dissolved Gases in Aquatic Environments With In Situ Mass Spectrometry", Environ. Sci. Technol., vol. 43, pp. 5014-5021.
Camilli, R., et al., (2007), "Characterizing Marine Hydrocarbons With In-Situ Mass Spectrometry", MTS, 7 pages.
Camilli, R., et al., (2010), "Tracking Hydrocarbon Plume Transport and Biodegradation At Deepwater Horizon", Science, vol. 330, pp. 201-204.
Chung, H.M., et al., (1988), "Origin of Gaseous Hydrocarbons in Subsurface Environments: Theoretical Considerations of Carbon Isotope Distribution", Chemical Geology, vol. 71, pp. 97-103.
Crovetto, R., et al., (1982), "Solubilities of inert Gases and Methane in H2O and in D2O In The Temperature Range of 300 to 600 K", J. Chem. Phys., vol. 78(2), pp. 1077-1086.
Dunn-Norman, S., et al., (2004), "Reliability of Pressure Signals In Offshore Pipeline Leak Detection", Dept. of The Interior, MMS TA&R Program, pp. 1-86.
Fomel, S., et ale (2007), "Poststack Velocity Analysis by Separation and Imaging of Seismic Diffractions", Geophysics, vol. 72(6), pp. U89-U94.
Heaton, T.H.E., et al., (1981), "Excess Air" in Groundwater, J. Hydrol., vol. 50, pp. 201-216.
Hohl, D., et al., (2010), "Energy, Environment and Climate Directorate White Paper", DCO Energy, Environment and Climate Workshop, 38 pages.
Holbrook, W.S., et al., (2003), "Thermohaline Fine Structure in an Oceanographic Front From Seismic Reflection Profiling", Science, vol. 301, pp. 821-824.
Huc, A.Y., (2003), "Petroleum Geochemistry At The Dawn of The 21st Century", Oil & Gas Science and Technology, vol. 58(2), pp. 233-241.
IP.com, (2012), "Detection of Underwater Hydrocarbon and Related Fluid Seeps Using Reflection Seismic Data", 3 pages.
Jakuba, M.V., et al., (2011), "Toward Automatic Classification of Chemical Sensor Data From Autonomous Underwater Vehicles", IEEE/RSJ International Conference on Intelligent Robots and Systems, pp. 4722-4727.
Kharaka, Y.K., et al., (1988), "The Solubility of Noble Gases in Crude Oil at 25-100 C", Applied Geochemistry, vol. 3, pp. 137-144.
Kinsey, J.C., et al., (2011), "Assessing the Deepwater Horizon Oil Spill With the Sentry Autonomous Undetwater Vehicle", IEEE/RSJ International Conference on Intelligent Robots and Systems, pp. 261-267.
Lamontagne, R.A., et al., (2001), "Response of METS Sensor To Methane Concentrations Found On The Texas-Louisiana Shelf In The Gulf of Mexico", Navel Research Laboratory, 14 pages.
Larter, S.R., et al., (1995), "Reservoir Geochemistry: Methods, Applications and Opportunities", The Geochemistry of Reservoir, Geological Society Special Publication No. 86, pp. 5-32.
Liu, W., et al., (2007), "Ternary Geochemical-Tracing System In Natural Gas Accumulation", Science In China Series D: Earth Sciences, vol. 50(10), pp. 1494-1503.
Macdonald, I.R., et al., (2002), "Transfer of Hydrocarbons From Natural Seeps To The Water Column and Atmosphere", Geofluids, vol. 2, pp. 95-107.
Makris, N.C., (2006), "Fish Population and Behavior Revealed By Instantaneous Continental Shelf-Scale Imaging", Science, vol. 311, pp. 660-663.
Mangelsdorf, K., et al., (2011), "Microbial Lipid Markers Within and Adjacent To Challenger Mound In The Beigica Carbonate Mound Province, Porcupine Basin, Offshore Ireland (IODP Expedition 307)", Marine Geology, vol. 282, pp. 91-101.
Narr, W., et al., (1984), "Origin of Reservoir Fractures In Little Knife Field, North Dakota", The American Association of Petroleum Geologists Bulletin, vol. 68(9), pp. 1087-1100.
Ozgul, E., (2002), "Geochemical Assessment of Gaseous Hydrocarbons: Mixing of Bacterial and Thermogenic Methane In The Deep Subsutface Petroleum System, Gulf of Mexico Continental Slope", Texas A&M University, Thesis, pp. 1-167.
Pinti, D.L., et al., (1995), "Noble Gases In Crude Oils From The Paris Basin, France: Implications For The Origin of Fluids and Constraints On Oil-Water-Gas Interactions", Geochimica et Cosmochimica Acta, vol. 59(16), pp. 3389-3404.
Prinzhofer, A., et al., (2003), "Gas Isotopes Tracing: An Important Tool For Hydrocarbons Exploration", Oil & Gas Science and Technology, vol. 58(2), pp. 299-311.
Ruddick, B., et al., (2009), "Wear Column Seismic Images As Maps of Temperature Gradient", Oceanography, vol. 22(1), pp. 192-205.
Sackett, W.M., (1977), "Use of Hydrocarbon Sniffing In Offshore Exploration", Journal of Geochemical Exploration, vol. 7, pp. 243-254.

(56) References Cited

OTHER PUBLICATIONS

Smith, S.P., et al., (1985), "Noble Gas Solubility in Water At High Temperature", GCA, vol. 46, p. 397.
Valentine, D.L., et al., (2010), "Asphalt Volcanoes As A Potential Source of Methane To Late Pleistocene Coastal Waters", Nature Geoscience, vol. 3, pp. 345-348.
Zaikowski, A., et al., (2010), "Noble Gas and Methane Partitioning From Ground Water: An Aid To Natural Gasa Exploration and Reservoir Evaluation", Geology, vol. 18, pp. 72-74.
Zartman, R.E., et al., (1961), "Helium, Argon, and Carbon In Some Natural Gases", Journal of Geophysical Research, vol. 66, No. 1, pp. 277-306.
Zhang, Y., et al., (2011), "A Peak-Capture Algorithm Used On An Autonomous Underwater Vehicle In The 2010 Gulf of Mexico Oil Spit Response Scientific Survey", Journal of Field Robotics, vol. 28(4), pp. 484-496.
Dalgleish, F.R., et al., (2013), "Towards Persistent Real-Time Autonomous Surveillance and Mapping of Surface Hydrocarbons", OCT 24241, pp. 1-18.
Chase, C., et al., (2010), "Real-Time Monitoring of Oil Using Ultraviolet Filter Fluorometry", Sea Technology, pp. 45-50.
ASTM International (2011), "Standard Practices for Sampling of Waterborne Oils", Designation: D4489-95 (Reapproved 2011), pp. 1-4.
Caccia, M. et al., "Design and Exploitation of an Autonomous Surface Vessel for the Study of Sea-Air Interactions," Proceedings of the 2005 IEEE, Barcelona, Spain, pp. 3582-3587 (Apr. 2005).
Camilli, R. et al., "Integrating In-situ Chemical Sampling with AUV Control Systems," 2004 MTTS/IEEE Techno-Ocean Conf., Piscataway, NJ, pp. 101-109 (Nov. 9-12, 2004).
Chang, W.J. et al., "Evaluation of Boat Deployable Thin Film Oil Samplers," XP055216718, Offshore Technology Conf., Dallas, TX, 20 pgs. (1984).
Fries, D. et al., "Solar Robotic Material Sampler System for Chemical, Biological and Physical Ocean Observations,"XP032075878, *IEEE*, 5 pgs. (Sep. 19, 2011).
Leighton, J., "System Design of an Unmanned Aerial Vehicle (UAV) for Marine Environmental Sensing," XP055217103, S.B., http://www.dtic.mil/docs/citations/ADA573151, Massachusetts of Technology, 70 pgs. (Feb. 2013).
Robinson, B., "A Guide to the Sampling and Analysis of Waters, Wastewaters, Soils and Wastes," Environment Protection Authority, State Government of Victoria, 54 pgs. (Mar. 2000).
Abrams, M.A., et al., (2010), "Geochemical Evaluation of Ocean Surface Slick Methods to Ground Truth Satellite Seepage Anomalies For Seepage Detection", *AAPG Convention, Search and Discovery Article #40604*, pp. 1-18.
ASTM International, (2011), "Standard Practices for Sampling of Waterborne Oils", pp. D4489-95.
Autonomous Surface Vehicles Limited, (2015), ASV Global, Retrieved Oct. 9, 2015, from C-Cat 5 Datasheet: http://www.asvglobal.com, pp. 1-4.
Caccia, M., et al., (2005), "Sampling Sea Surfaces with SESAMO", *IEEE Robotics & Automation Magazine*, pp. 95-105.
Chase, C.R., et al., (2010), "Real-Time Monitoring of Oil Using Ultraviolet Filter Fluorometry", *Sea Technology*, pp. 1-9.
Chelsea Technologies Group, Ltd., (2015), "UV AquaTracka Fluorometer", Retrieved Oct. 9, 2015 from http://www.chelsea.co.uk/allproduct/marine/fluorometers/uv-aquatracka-fluorometer, 2 pages.
CSafe Global (2015), AcuTemp AX56L, Retrieved Oct. 9, 2015 from http://www.acutemp.com/products-AcuTemp-AX56L, 1 page.
Dalgleish, F. R., et al., (2013), "Towards Persistent Real-Time Autonomous Surveillance and Mapping of Surface Hydrocarbons", *OTC 24241*, Houston: Offshore Technology Conference, pp. 1-18.
Engineering Toolbox, The, (2015) "The Engineering Toolbox—Liquids—Densities", Retrieved Oct. 9, 2015 from The Engineering Toolbox: http://www.engineeringtoolbox.com/liquids-densities-d_743.html, 8 pages.
National Oceanic and Atmospheric Administration, (2012), "Open Water Oil Identification Job Aid", Seattle: US Dept. of Commerce, pp. 1-52.

\* cited by examiner

METHOD AND SYSTEM FOR IDENTIFYING AND SAMPLING HYDROCARBONS WITH BUOYS

CROSS-REFERENCE TO RELATED APPLICATION

This application claims the benefit of U.S. patent application Ser. No. 14/752,030 filed Jun. 26, 2015; U.S. Provisional Patent Application Ser. No. 62/026,449 filed Jul. 18, 2014; U.S. Provisional Patent Application 62/180,987 filed Jun. 17, 2015; U.S. Provisional Patent Application 62/190,089 filed Jul. 8, 2015; and U.S. Provisional Patent Application 62/190,999 filed Jul. 10, 2015, the entirety of each is incorporated by reference herein.

FIELD OF THE INVENTION

This invention relates generally to the field of hydrocarbon exploration and development. Specifically, the invention relates to operations for exploring and developing hydrocarbons (e.g., oil and/or gas) with one or more remote devices, such as buoys.

BACKGROUND OF THE INVENTION

Hydrocarbon reserves are becoming increasingly difficult to locate and access, as the demand for energy grows globally. As a result, various technologies are utilized to collect measurement data and then to model the location of potential hydrocarbon accumulations. The modeling may include factors, such as (1) the generation and expulsion of liquid and/or gaseous hydrocarbons from a source rock, (2) migration of hydrocarbons to an accumulation in a reservoir rock or to the surface, (3) a trap and a seal to prevent significant leakage of hydrocarbons from the reservoir. The collection of data, such as marine surveying approaches, may be beneficial in modeling potential location for subsurface hydrocarbon accumulations.

One conventional marine surveying approach involves remote sensing an area of interest. For example, reflection seismic is the dominant remote sensing technology for the identification of hydrocarbon accumulations. This approach has been successful in identifying structures that may host hydrocarbon accumulations, and may also be utilized to image the hydrocarbon fluids within subsurface accumulations as direct hydrocarbon indicators (DHIs). However, this approach may lack the required fidelity to provide accurate assessments of the presence and volume of subsurface hydrocarbon accumulations due to poor imaging of the subsurface, particularly with increasing depth where acoustic impedance contrasts that cause DHIs are greatly diminished or absent. Further, non-seismic hydrocarbon detection technologies, such as potential field methods like gravity or magnetics or the like, provide coarse geologic subsurface controls by sensing different physical properties of rocks, but lack the fidelity to identify hydrocarbon accumulations. As such, the conventional approaches may merely provide guidance on where a basin seismic survey should be conducted, but do not significantly improve the ability to confirm the presence of hydrocarbon seeps or subsurface hydrocarbon accumulations.

Other conventional marine surveying may involve the use of manned vessels or vehicles to collect samples. See, e.g., American Standards and Testing Association's Standard Practice D4489. However, such sampling approaches are expensive due to the vessel deployment requirements and the number of samples is limited by the amount of time a vessel and its crew can remain on the body of water to perform operations. Further, samples obtained from the manned vessel's operations may fail to obtain samples from a target of interest or include samples that are compromised due to marine vessel traffic or other disturbances. As a result, the conventional approaches may provide a limited coverage area, may require certain amounts of lead time to prepare and deploy the vessel and crew, may involve additional verification steps to confirm a target of interest is present because of the delays in deployment, and may provide limited flexibility for adjusting a course plan or trajectory during operations (e.g., real-time or concurrent adjustments). As such, manned marine surveying approaches have various limitations for surveying operations.

Yet another approach for marine surveying may include remote sensing coupled with a sampling operations. This approach may be used to identify possible features of interest (e.g., oil slicks from seeps, red tide or a chemical pollutant) or wildlife (e.g., invasive, rare, threatened or endangered species locations). The remote sensing may be performed indirectly (e.g., with satellite or airborne imaging) or directly (e.g., via observations and sampling from a marine vessel). Then, a marine vessel can be deployed with a manned crew to determine the location of the observation and to obtain samples. However, similar to the discussion above regarding manned approaches, the deployment of a marine vessel may be time consuming and expensive to operate. Further, because the deployment involves processing remote sensing data and the deployment may involve delays, this approach may not be able to locate the ephemeral feature, as it is not performed in a timely manner. That is, the target or feature may have aged, dissipated, or moved to a different location as a result of changes in conditions, such as currents and/or wind. In addition, a chemical associated with the target may have to involve high concentrations to be detected and may have to be at the surface to be discernable via satellite or aircraft. Also, this approach may have difficulties in addressing and overcoming limitations from noise (e.g., signal to noise ratio in processing of the data). These difficulties may be a result of the problems of determining background levels present within a certain body of water and identifying anomalies as compared to the background levels, and then to locate anthropogenic sources that may not persist over time. Thus, this approach has additional limitations.

As a result, enhancements to marine surveying approaches are needed. In particular, marine surveying may include obtaining samples of biological origin, hydrocarbons and/or chemicals, which may be used to enhance hydrocarbon exploration, hydrocarbon development, and/or environmental monitoring of bodies of water with one or more buoys. The obtained samples may also provide biodiversity data at different trophic levels, through the analysis of environmental deoxyribonucleic acid (eDNA), which may provide useful information on the impact of an event or ongoing anthropomorphic features, for waterborne pathogens and for studying invasive or endangered species. These techniques may efficiently obtain samples from waterborne liquid hydrocarbons for indicators of a working hydrocarbon system in exploration areas, which may then be used to enhance basin assessment and to high-grade areas for further exploration.

SUMMARY OF THE INVENTION

In one embodiment, a method for identifying and sampling target materials with one or more buoys is described.

The method includes: deploying one or more buoys to a location in a body of water, wherein at least one of the one or more buoys has a buoy monitoring section that includes a measurement component and a sampling component; obtaining measurement data associated with the body of water with a measurement component; determining whether target material is present in the measurement data, wherein the target material comprises one or more of biological, chemical, hydrocarbon and any combination thereof; and obtaining a sample of the target material with the sampling component; and storing the obtained sample.

In yet another embodiment, a buoy monitoring and sampling system is described. The system includes a buoy having a buoy monitoring section that includes a measurement component and a sampling component; wherein the measurement component is configured to obtain measurement data associated with the body of water and to identify a target material; and the sampling component is configured to obtain a sample.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION OF THE PREFERRED EMBODIMENTS

Figure 1A:
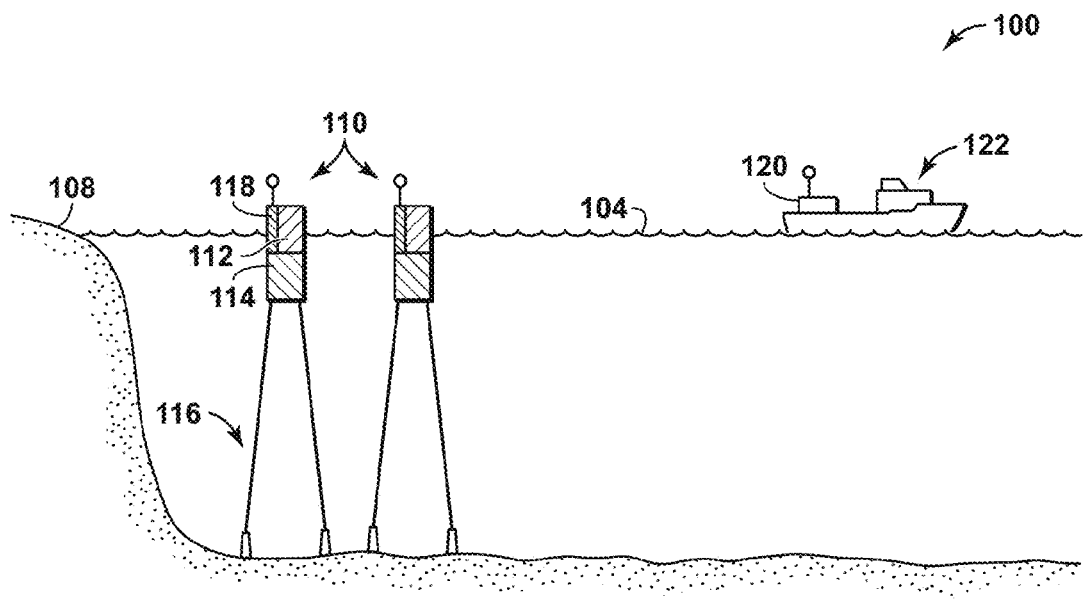
FIGS. 1A to 1E are diagrams of a buoy monitoring system in accordance with an exemplary embodiment of the present techniques.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

The articles "the", "a" and "an" are not necessarily limited to mean only one, but rather are inclusive and open ended so as to include, optionally, multiple such elements.

As used herein, "marine", means any body of water. The bodies of water may include oceans, seas, gulfs, lakes, rivers and streams, for example.

As used herein, the term "hydrocarbon system" refers to the relationships between required components and the processes required for the presence of any subsurface hydrocarbon accumulation as described by Magoon and Beaumont. See, e.g., Magoon and Beaumont, The Petroleum System—from source to trap: AAPG Memoir 60 (1994). Subsurface hydrocarbon accumulations in a sedimentary basin include (1) the presence of a source rock from which hydrocarbons can be generated, (2) the burial of the source rock to sufficient temperatures and pressures to result in the generation and expulsion of liquid hydrocarbons from a source rock (source maturity), (3) presence of a reservoir of sufficient adequacy to store hydrocarbons, (4) migration of liquid hydrocarbons to and accumulation in a reservoir, and (5) a trap and a seal that prevents significant leakage of hydrocarbons from the reservoir. The relative timing of each of these components and processes are utilized to determine the existence of any accumulation.

The present techniques provide enhancements to marine surveying (e.g., hydrocarbon exploration, hydrocarbon development, environmental assessment and/or surveying techniques), which utilizes one or more buoys to collect samples. The one or more buoys may be used concurrently with the performance of remote sensing over a region to identify potential locations of target materials (e.g., potential biological, chemical and/or hydrocarbon locations). Also, the buoys may be used to collect samples from the locations on the body of water. The concurrent operations may include obtaining and transmitting the remote sensing data or information derived from the remote sensing data to one or more buoys. Then, one or more of the buoys may be deployed to the location (e.g., biological, chemical and/or hydrocarbon location) for sampling operations.

In the present techniques, the remote sensing data is acquired, interpreted and communicated in near real-time or concurrently. The term, "near real-time", means that information is obtained, processed, and acted upon prior to buoy deployment (e.g., one or two weeks prior to buoy deployment) and/or during the buoy deployment. The term includes time delay between the acquisition of the remote sensing data and the time at which such data can be acted upon. The transmitted location may be used to move the buoy to any identified location (e.g., suspected biological, chemical and/or hydrocarbon location) for sampling. The term, "concurrent" or "concurrently", means that the information is obtained, processed, and acted upon at time intervals that overlap with each other. That is, the acquisition, processing and transmission of the remote sensing data may be performed within a first time interval and the buoy may be performing operations for a second time interval (e.g., performing the deployment stage, sampling stage, etc.). The first time interval and the second time interval overlap during the performance of the method.

Beneficially, such techniques provide enhancements over conventional approaches. For example, environmental information is typically not obtained for a regional scale, not appropriately evaluated or sampled and may not be integrated with hydrocarbon information. Also, the present techniques combine remote sensing with buoy deployment and sampling to create a less expensive means of evaluating regions of interest by monitoring target materials, such as hydrocarbons, biodiversity and water body chemistry.

In one or more embodiments, the present techniques utilize a combination of satellite and/or airborne remote sensing techniques along with one or more buoys to characterize and map the body of water in concurrent operations. The combination of remote sensing techniques along with buoys that obtains samples provides a more detailed characterization of the environmental features of the marine or aquatic environment over many different scales. The data collected may include one or more of biological, chemical, or hydrocarbon data and any combination thereof.

The remote sensing operations (e.g., satellite and/or airborne) may include synthetic aperture radar (SAR) along with other techniques. Remote sensing involves obtaining measurements over the body of water. As an example, remote sensing refers to the use of sensors mounted on orbiting satellites to acquire synthetic aperture radar (SAR) images and/or other types of data that indicate the area of interest. The remote sensing data may be integrated with other data to further enhance the process and provide different scales of information about a region of interest. For example, the remote sensing data may be combined with measurement data, which may be provided from a marine vessel (e.g., vessels performing other duties such as seismic and acoustic imaging, multibeam echosounder, side-scan sonar, sub-bottom profiler; magnetic and gravity surveying) and sampling data from the buoy.

The sampling is performed by a buoy, which may include autonomous control to operate the performance of various tasks. The buoy may include one or more components configured to perform various tasks, such as acquiring samples and/or detecting chemical, biological or physical anomalies, which may be indicative of changes in environmental factors. For example, the buoy may include a sampling component, which is utilized with the measurement component, communication component and/or location modules to enhance operation of the system.

In one or more embodiments, the present techniques may be used to perform enhanced marine surveying. The method may include obtaining a potential location of target materials using remote sensing data, acoustic measurements, shipboard measurements or other similar data; based on the remote sensing data deploying one or more buoys to the potential location (e.g., biological, chemical and/or hydrocarbon location); and obtaining a sample of target materials (e.g., water, biological material, chemicals, hydrocarbons and/or other target materials) with the buoy. The method may include performing remote sensing (e.g., synthetic aperture radar (SAR)) in a survey area to identify the potential location to sample. The target material may include information for biodiversity at different trophic levels, through analysis of using environmental deoxyribonucleic acid (eDNA). As an example, the target materials may include waterborne liquid hydrocarbons and/or aquatic organisms in a marine environment.

Further still, in some other embodiments, the present techniques involve an autonomous buoy monitoring configuration. In the autonomous buoy monitoring system, one or more buoys may include measurement components, sampling components, communication components and/or location components to enhance operation of the system. The system and method include one or more buoys that use sensors (e.g., part of the measurement components) to monitor its integrity or operation (e.g., anchor failure, storage containers are used or below a threshold, boom splitting and/or failure, or buoy sinking). In addition, the system may include one or more buoys that are equipped with sensors (e.g., part of the measurement component) that may determine whether one of the portions of the system is being contacted by target material (e.g., biological, chemical and/or hydrocarbons). If any of the buoy events occur, one or more of the buoys may send a communication to a command unit, which may be a marine vessel or airborne vessel that deploys and retrieves the buoys, alerting the control unit of the situation. The control unit may manage notifications or other actions to have the repair and/or replacement of the event associated with the buoy.

The sampling component may include one or more different components to obtain samples of target materials. For example, as noted in U.S. Patent Application Nos. 62/026,449 and 62/180,987, each of which is incorporated herein by reference, various mechanisms for sampling materials are described. One or more of these sample collection and storage techniques may also be utilized with the buoy system described herein.

The buoy system may include a configuration of buoys that may be deployed to cover a specific target location. While the buoys may be permitted to drift in certain embodiments, the buoy system is preferably disposed into a fixed location. This location may be near an area where slicks have been identified through remote sensing. The configuration of buoys may be determined based on the locations where target materials (e.g., waterborne hydrocarbons) are expected to drift once they reach the surface of the body of water. This determination may be based on wind, currents and other weather or environment conditions. Various aspects of the present techniques are described further in FIGS. 1A to 11.

FIGS. 1A to 1E are various diagrams 100, 130, 140, 150 and 160 of buoy monitoring systems in accordance with an exemplary embodiment of the present techniques. For example, FIG. 1A is a diagram 100 of a buoy monitoring system in accordance with an exemplary embodiment of the present techniques. The buoy monitoring system may include one or more buoys, such as buoys 110, that are in communication with a command unit 120, which is shown disposed on a ship 122. The buoys and the ship 122 may be disposed in a body of water 104 and the booms may be deployed to near a region of interest for a target material adjacent to a shore 108.

In this diagram 100, buoys may be deployed in a specific configuration to detect target materials (e.g., hydrocarbons floating on the surface of the body of water 104). For example, buoys 110 may include a floating section 112 that has a portion partially submerged in the body of water 104 and a portion that extends out of the water 104, a skirt and ballast section 114 that is located in the body of water 104, and an anchor section 116 utilized to secure the buoy in a relatively fixed location. The floating section 112 is configured to maintain target materials from entraining over the buoy, and the skirt and ballast section 114 is configured to maintain target material from entraining under the buoy. Combined the floating section 112 and the skirt and ballast section 114 are utilized to either contain or divert the target materials. The anchor section 116 may include one or more anchors and associated lines to secure the anchors to the skirt and ballast section 114. If more than one buoy is used, each buoy 110 may include these different sections 112, 114 and 116.

Further, the buoy 110 may include a buoy monitoring section 118 that is utilized to determine whether a buoy operation event has occurred. The buoy monitoring section 118 may include power components, communication components, sampling components, storage components and/or measurement components. Each of these components may be located within a secure compartment to minimize exposure to water or other environmental conditions. Further, if more than one buoy is used, the buoy monitoring section 118 may include different components in each. For example, one may include the power components, communication components, sampling components, storage components and/or measurement components, while another buoy may include power components, sampling components, storage components and/or measurement components. The specific configuration may be adjusted based on the number of buoys and redundancy considerations. Further, the buoy monitoring section 118 may include a portion of the components integrated with the floating section 112, while another portion of the components may be disposed into a tethered floatation vessel or vessels that is able to maintain these components separate from the buoy.

The power components may include a battery, wind, wave, and/or solar powered equipment. The different components or modules may be powered from the power component or may include separate power sources for each of the respective components or modules. Also, the different components and modules may also utilize a separate power source as a redundant power supply in certain embodiments.

The communication component may include communication equipment that is utilized with one or more antennas to communicate with one or more of other buoys, internal components or modules, and/or the command unit 120. The communication equipment may utilize technologies, such as radio, cellular, wireless, microwave or satellite communication hardware and software. Also, the communication equipment may include and utilize any of a variety of known protocols to manage the exchange of information (e.g., Ethernet, TCP/IP, and the like). The communication equipment utilized may depend on the specific deployment locations and configuration. For example, if two or more buoys are located in close proximity to each other, one buoy may include satellite communication equipment along with radio or wireless communication equipment, while the other buoys may include only radio or wireless communication equipment. In this manner, the buoy with the satellite communication equipment may handle communication to the command unit 120 for the other buoys. Alternately, each buoy may include each of measurement components and/or modules and communication components to operate independently.

The measurement component may include various modules that provide information relating to buoy operation events. For example, the measurement components may include a global positioning system (GPS) module and sensors that monitor buoy location over time; a target material sensing module and sensors that monitor for buoy contact with target material present near or on the surface of the water; a pressure module and sensors that alarm if the buoy sinks below the surface of the water; an air pressure module and sensors that alarm if the air-pressure inside and inflatable buoy is decreasing, and/or buoy integrity module and sensors to determine if the buoy is damaged. Each of these modules may be utilized as separate modules in communication with separate or shared sensors and/or a common module and sensor configuration.

The sampling component may include various modules that acquire samples of target materials. The sampling components may include various sensors and/or modules to identify the target materials (e.g., waterborne hydrocarbons). For example, the sensors and/or modules may include ultraviolet sensors, flow-through optical sensors, active ultraviolet modules, visible and infrared light cameras and/or electromagnetic radiation modules. Further, the sampling components may include various sensors or modules to acquire one or more samples of the target materials. For example, the sensors and/or modules may include sampling containers, sampling materials, passive or active flow-through modules, visible and infrared light modules, electromagnetic radiation modules and/or other sampling techniques.

The storage components may include various modules that acquire samples of target materials. The storage components may include various sensors and/or modules to store and maintained the samples of the target materials. For example, the sensors and/or modules may be configured to store the samples in individual compartments, which are isolated from each other to lessen any cross contamination. The storing of the samples may involve managing the storage temperature of the samples, which may be in the range between about −10° C. and about 10° C., for hydrocarbon samples and between about −10° C. and about −100° C., for biology samples. The storage components may be configured to store multiple samples over a deployment period that may range from weeks to months.

Further, the command unit 120 may be utilized as a central control mechanism to manage the one or more buoys disposed in the body of water, which may include different geographic areas. The command unit 120 may include power components, communication components and/or management components. The location of the command unit 120 is not dependent on the buoy locations. Accordingly, the command unit 120 may be disposed on a vessel, such as ship 122, to facilitate timely response to any buoy events. However, other embodiments may include the command unit 120 being located at an onshore location, on a platform, or even in a helicopter or plane.

Figure 1B:
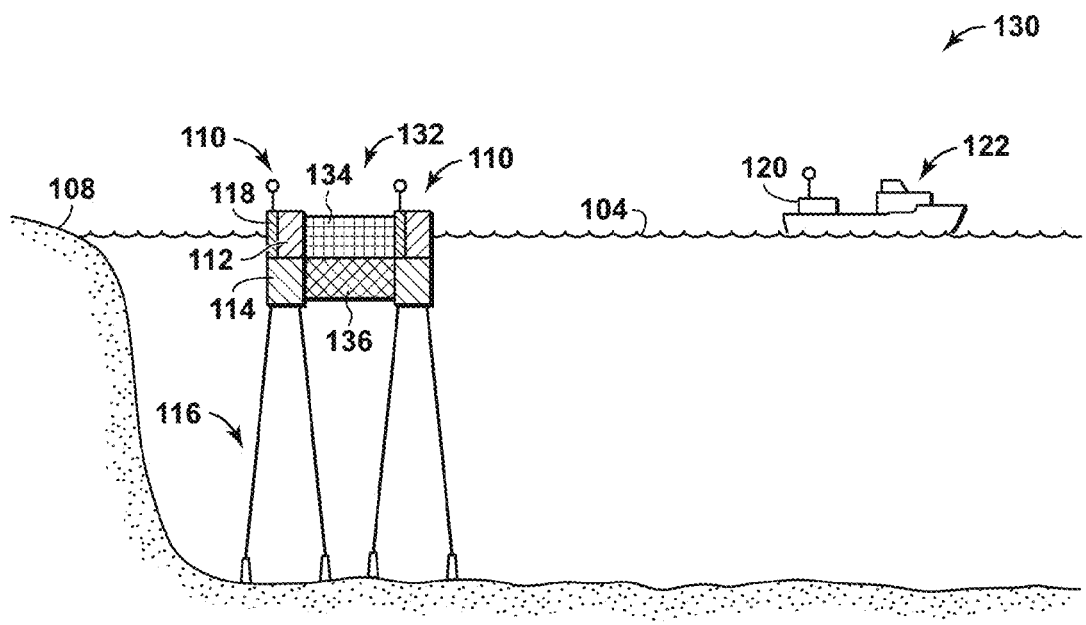

FIG. 1B is a diagram 130 of a buoy monitoring system having a boom 132 in accordance with an exemplary embodiment of the present techniques. While the buoy monitoring system may include many of the same components, as noted above in FIG. 1A, this system may include one or more booms, such as boom 132 having a surface section 134 and a subsurface section 136, which is secured to two buoys. The booms may be disposed in a body of water 104 and the booms may be deployed to further enhance the identification and collection of samples of a target material.

Booms may be connected together to manage the target materials floating on and/or near the surface of the body of water 104. For example, boom 132 may include a surface section 134, which is secured to the floating sections of two different buoys. This surface section may have a portion partially submerged in the body water 104 and a portion that extends out of the body of water 104. Similarly, the subsurface section 136 may be disposed below the surface of the body of water 104 and may be secured to the skirt and ballast sections of the same buoys coupled to the surface section 134. The surface section 134 may be configured to maintain and manage target materials for sample collection, while the subsurface section 136 may be configured to maintain the surface section or manage target materials from entraining under the boom. Combined, the surface section 134 and the subsurface section 136, may be utilized to manage or divert the target materials for sampling operations. In certain configurations, the boom 132 may also include an anchor section (not shown), which may include one or more anchors and associated lines to secure the anchors to the sections. If more than one boom is used, each boom may include these different sections 134 and 136.

Figure 1C:
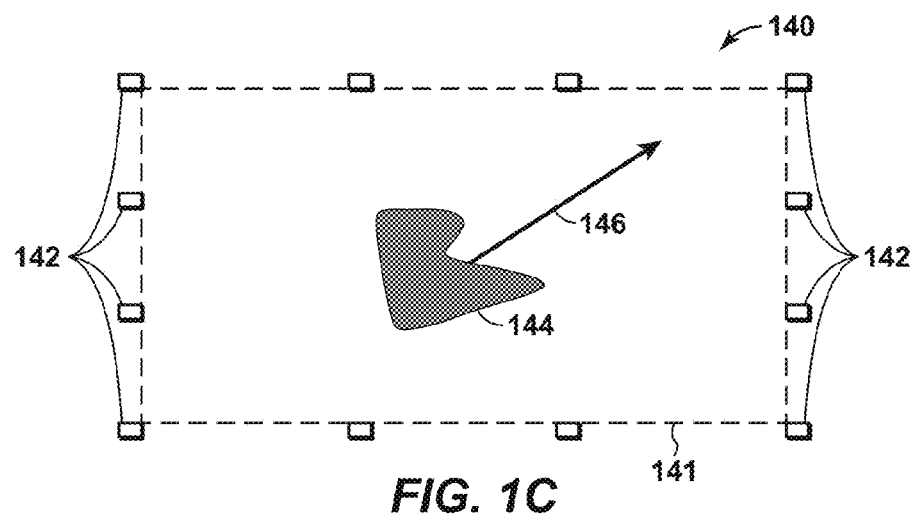

FIG. 1C is a diagram 140 of a buoy monitoring system having various buoys 142 deployed in a configuration over a region of interest 141 in accordance with an exemplary embodiment of the present techniques. In this diagram 140, a target material 144 is initially detected within a region of interest 141. This region of interest 141 may be defined by the area within the deployed buoys 142, which may be the buoys described in FIG. 1A. For example, remote sensing, such as SAR imagery, may be used to detect hydrocarbons on the surface of a body of water. The buoys 142 may be disposed around the periphery of the target material 144 to form the interface area for the target material based on the expected movement. The configuration of the buoys may be specific to the expected drift of the target materials or may be specific to the region of interest if the drift direction is not known (e.g., buoys are located in various possible drift directions). For example, the deployed configuration of the buoys 142 is based on the predicted movement of the target material 144, as shown by arrow 146.

Figure 1D:
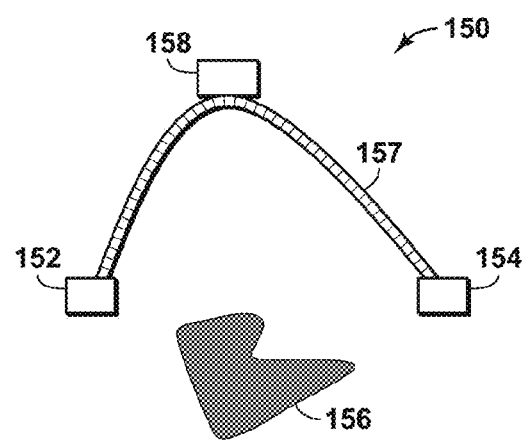

FIG. 1D is a diagram 150 of a buoy monitoring system having various buoys 152 and 154 deployed in a configuration over a region of interest in accordance with an exemplary embodiment of the present techniques. In this diagram 150, a target material 156 is drifting toward the buoys 152 and 154, which have a boom 157 secured to each of the buoys 152 and 154. Each of these buoys 152 and 154 may be embodiments of the buoys described in FIG. 1A. In addition, this diagram 150 includes a sampling component 158, which may be a component of one of the buoys 152 and 154 or separate component. The sampling component 158 may use one or mechanisms to collect samples (e.g., via deployment and retrieval of a sampling material, via a fluid capture technique, via a solid phase extraction (SPE) technique and/or the like.

Figure 1E:
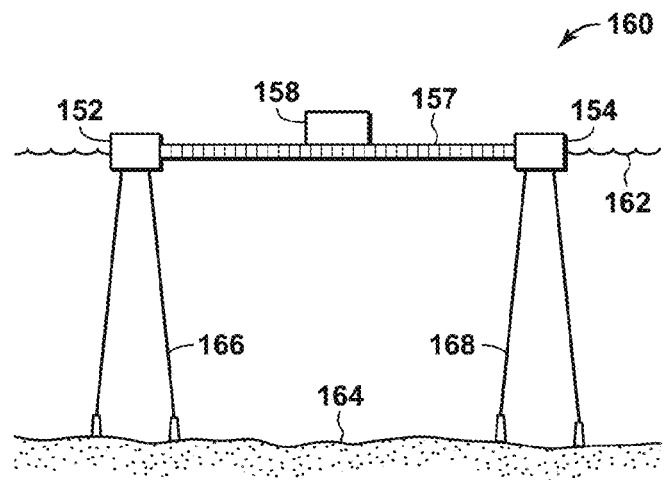

FIG. 1E is a diagram 160 of an alternative view of the buoy monitoring system having various buoys 152 and 154 deployed in a configuration over a region of interest in accordance with an exemplary embodiment of the present techniques. In this diagram 160, the buoys 152 and 154, boom 157 and sampling component 158 are disposed on the surface 162 of a body of water. Each of the buoys 152 and 154 may have anchor sections, such as anchor sections 166 and 168, disposed on the floor 164 of the body of water. The anchor sections are configured to maintain a fixed position for the buoys 152 and 154. After the deployment, the samples may be collected and analyzed.

Figure 2:
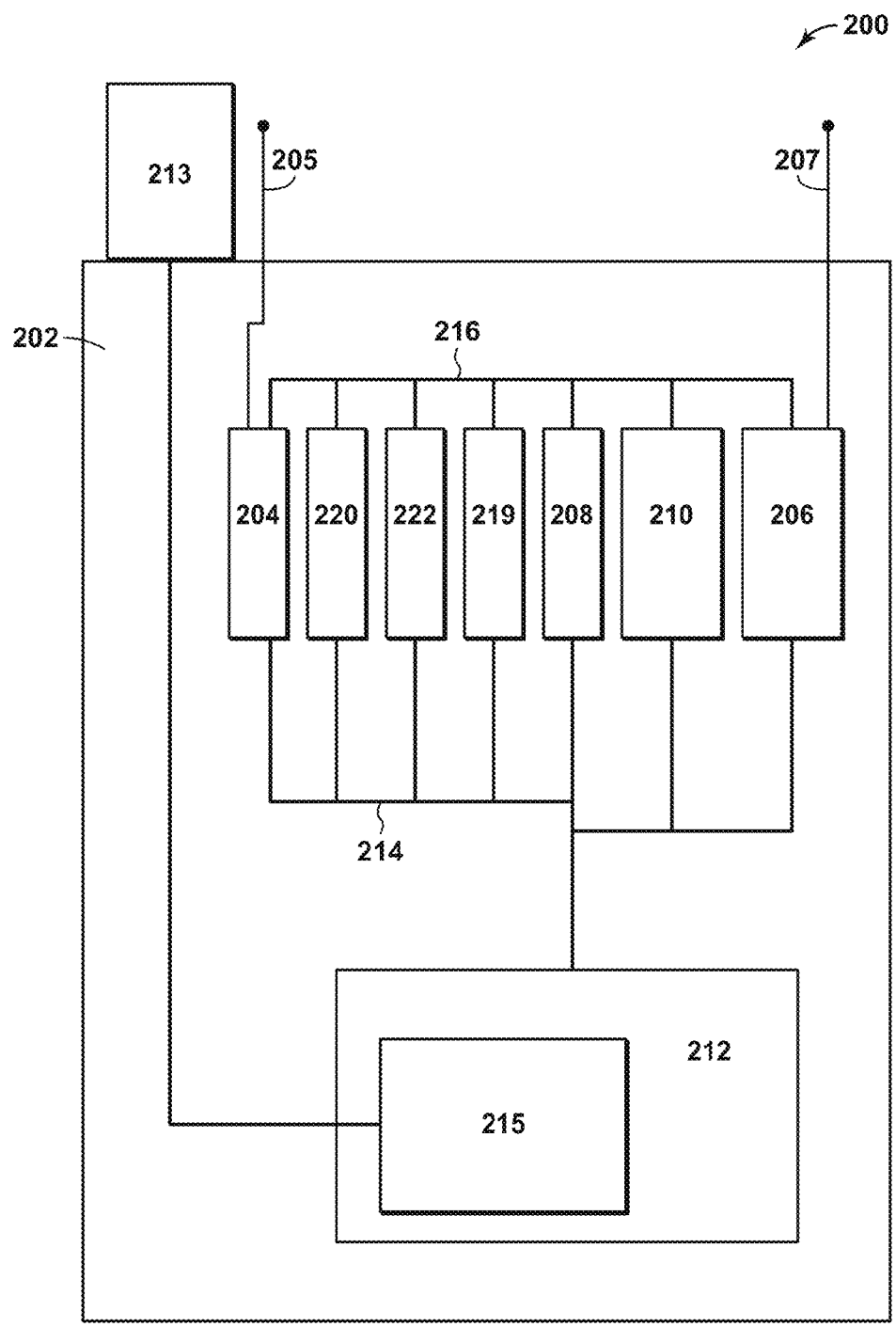
FIG. 2 is a diagram of an exemplary buoy monitoring section in accordance with an exemplary embodiment of the present techniques.

FIG. 2 is an exemplary buoy monitoring section 200, which may be one embodiment of the buoy monitoring section 118 of FIG. 1A. In this FIG. 2, the exemplary buoy monitoring section 200 includes a housing 202. The housing 202 may be a sealed housing that protects the measurement component, storage component and communication component from the environmental conditions. The housing may enclose a global positioning system (GPS) module 204 and associated GPS antenna 205, a communication component 206 and associated communication antenna 207, a pressure module 208, a target sensing and integrity module 210, air-pressure module 219 and a power component 212. Further, the housing may include a storage component 220 and a sampling component 222. The modules and components are provided power from the power component 212 via power distribution lines 214. Similarly, the different modules and components may communicate with each other via communication lines 216. This embodiment utilizes a central power and communication lines to manage the operation in an efficient manner.

To operate, the power component 212 may be utilized to supply power to the system (GPS) module 204, communication component 206, pressure module 208, target sensing and integrity module 210, air-pressure module 219, storage component 220 and a sampling component 222. In this embodiment, the power component 212 includes a solar module 213 and batteries 215. The batteries 215 may provide power via the power distribution lines 214, which may include one or more cables, as an example. The solar module may include solar panels and associated equipment that are utilized to convert solar rays into power, which may be used to power the modules and components and also to recharge the batteries 215.

For communication, the communication component 206 is utilized to exchange information between the different modules and components and/or the command unit via the communication lines 216 and the communication antenna 207. The communication component 206 may utilize the communication lines 216 to handle the exchange of information, such as measured data, status indications or other notifications, between the modules, such as the GPS module 204, pressure module 208, target sensing and integrity module 210, air-pressure module 219, storage component 220 and a sampling component 222. The communication line 216 may include a bus, Ethernet cable, fiber optics or other suitable physical connection. In an alternative embodiment, the communication between modules may be via a wireless connection. Similarly, the communication protocol may be any protocol known to those skilled in the art.

To monitor for buoy operation events, the GPS module 204, the pressure module 208, the air-pressure sensing and monitoring module 219, storage component 220 and target sensing and integrity module 210 may be utilized to measure parameters associated with the operation of the buoy. For example, the GPS module 204 may be utilized to determine whether the current buoy location has changed above a certain threshold relative to the initial buoy location. This may be performed by comparing the buoy location at a first and second time period. The movement threshold may be associated with a specific linear distance to allow for different currents and wave action. For instance, the movement threshold may be less than 25 feet, 50 feet or even 75 feet. This movement threshold may be adjusted based on the GPS modules spatial sensitivity and/or the length of the lines utilized to secure the buoy. As another example, the pressure module 208 may be utilized to determine the flotation status of the buoy (e.g., if the current buoy flotation status has changed relative to a certain floatation threshold or to the initial buoy flotation status). Similar to the GPS module, the current buoy flotation status may be compared for a first and second time period to determine the amount of change in the buoy flotation status. As another example, the air-pressure sensing and monitoring module 219 may be utilized to determine the pressure of air within the floating section. Certain buoy may be configured to inflate the floating section to float and operate efficiently. Further still, the target sensing and integrity module 210 may be utilized to determine the presence of target material (e.g., hydrocarbons, biology and certain chemistries) and/or whether the integrity of the buoy is intact. This module may compare the target material or integrity from a first time period to a second time period, respectively. The thresholds may be determined from set amounts (e.g., predetermined graphs based on the target material being detected). The amount of change in the target material status may indicate that target material is contacting the buoy, which may result in activating the sampling component, while the amount of change in the integrity threshold may indicate that the buoy has been damaged. As a specific example, the target sensing sensors (not shown) may be communicating with the target sensing and integrity module 210 may detect electrical resistance and provide an indication of the electrical resistance along respective lengths of the buoy (e.g., the floating section, which may be the floating section 112 as shown in FIG. 1). The electrical resistance indication (e.g., measured resistance or indication of the measured resistance) may be transmitted to and processed in the target sensing and integrity module 210, which may determine whether the target material is present. As yet another example, the storage component 220 may monitor the number of samples and/or the temperature of the samples. For example, the storage component may include a temperature module (not shown), which is utilized to determine the temperature of the storage containers associated with the buoy. The temperature module may be utilized to indicate whether the temperature has below or is above a preferred storage temperature. For example, the temperature module may provide a notification when the storage temperature of the samples is below about −10° C. and above about 10° C. for hydrocarbon samples and/or above about −10° C. and below about −100° C. for biology samples. Also, the storage components may include a storage container module, which is configured to determine the status of the storage containers. This module may indicate the number of samples obtained and/or the number of sample containers that have not been used.

To perform sampling operations, the sampling component 222 may include various modules to perform different types of sampling and provide the samples to the storage component 220. For example, the sampling component 222 may include a sampling material module configured to deploy a sampling material via a spool into the body of water and to retract the sampling material into the sampling container. Also, the sampling component 222 may include sampling tube module configured to obtain fluid into a sampling container or tube and seal the sampling container. The sampling component may also include a sample container module, which is utilized to manage the transfer of the sample containers with the storage component. These different modules are described further below.

The signatures measured from each of the target materials (e.g., seeps) may be analyzed according to disclosed methodologies and techniques herein to provide information about the environment (e.g., a hydrocarbon system). For example, for seeps, the information may be used to provide information about the environment. For example, for seeps the information may be used to discriminate between the different origins of hydrocarbons encountered at these seeps. In particular, methodologies and techniques disclosed herein may discriminate between hydrocarbons that have migrated directly to the surface without encountering a trap within which they can be accumulated (e.g., a first source) and hydrocarbons that have leaked from a subsurface accumulation (e.g., a second source). If the presence and volume of such a hydrocarbon accumulation can be identified, it is possible information about the hydrocarbons from such an accumulation can be determined for extraction. Further, the present techniques may be utilized to obtain biological and chemical data about the floor of the body of water and body of water, as well. For example, the present techniques may discriminate among the presence of different aquatic organisms, which may be utilized to indicate different aspects about the body of water.

As may be appreciated, natural seepage, aquatic organisms and/or chemistry of a body of water are often episodic, which makes the collection of samples of a target material difficult. A satellite image may indicate the likely presence of a target material, such as waterborne liquid hydrocarbons or aquatic organisms, but at a later time period (e.g., hours later) the waterborne liquid hydrocarbons may have dissipated and/or aquatic organisms may have migrated and may be undetectable upon arrival. For example, an area over a few square kilometers may have fairly consistent seepage, but the precise locations of the seeping origins and their waterborne liquid hydrocarbons may vary due to the meteorological or other environmental conditions.

Accordingly, each of the buoys may be configured to operate in various modes of operations. For example, once deployed, the buoy may enter a "target detection mode". In "target detection mode", the buoy may utilize various components to detect the target materials. As a specific example, to detect the waterborne liquid hydrocarbons, the buoy may use various sensors to identify the waterborne hydrocarbons, such as ultraviolet technology. See, e.g., Chase et al., 2010. Alternatively, the sensors may include flow-through optical sensors that are used to confirm the presence of hydrocarbons in the water. See, e.g., Dalgleish et al., 2013. As yet another, the buoy may have active ultra-violet modules that are configured to excite aromatic compounds in hydrocarbons and to detect resulting fluorescence emissions from the surface of the body of water. The buoy may also have electromagnetic radiation modules (e.g., visible and infrared light cameras) that can be used to investigate larger areas around the buoy to locate hydrocarbons, fauna and/or icebergs, for example.

Once the target materials are identified, then the buoy may enter into "target sampling mode". In this mode, the buoy deploys one of its sampling devices and collects a sample as appropriate for the type of target material to be collected. For example, the sampling material or tube is spooled back into the container, and the container is sealed shut. This sealing may isolate the sampling material or sampling vessel from other samples that are obtained to lessen any contamination. Then, the buoy may resume "target detection mode" and/or "target sampling mode". As an example, after the buoy collects a certain number of samples (e.g., two or more samples) from the target materials, the buoy may enter a "loitering mode" for a certain period of time, until further instructions are provided or until another target material is identified. This prevents oversampling from a single location.

Further, remote sensing may also be utilized to enhance the surveying. The target materials, such as waterborne liquid hydrocarbons or aquatic organisms, identified by satellite may be sporadic and not have a continuous presence for any considerable length of time. The use of buoys provides a mechanism to confirm the presence of the target material with some confidence prior to collecting a sample at its location. Without this ability, there is a high likelihood that a vast majority of the samples collected may contain no significant amount of target materials (e.g., hydrocarbons, biologic materials and/or chemical materials). As such, the buoy may have to spend considerable amounts of time searching for the target material (e.g., potential seepage locations and/or aquatic organisms).

As an example, the remote sensing may include the use of SAR technology. SAR images may be obtained for substantial amounts of the area of interest at different intervals. For example, the intervals may be two days, although the frequency of acquisition, resolution of images, and size and location of images may be adjusted for different applications. Once analyzed, buoys may be deployed, as appropriate, based at least partially on the information obtained from the SAR images. The method associated with one exemplary method is further described in FIG. 3.

Figure 3:
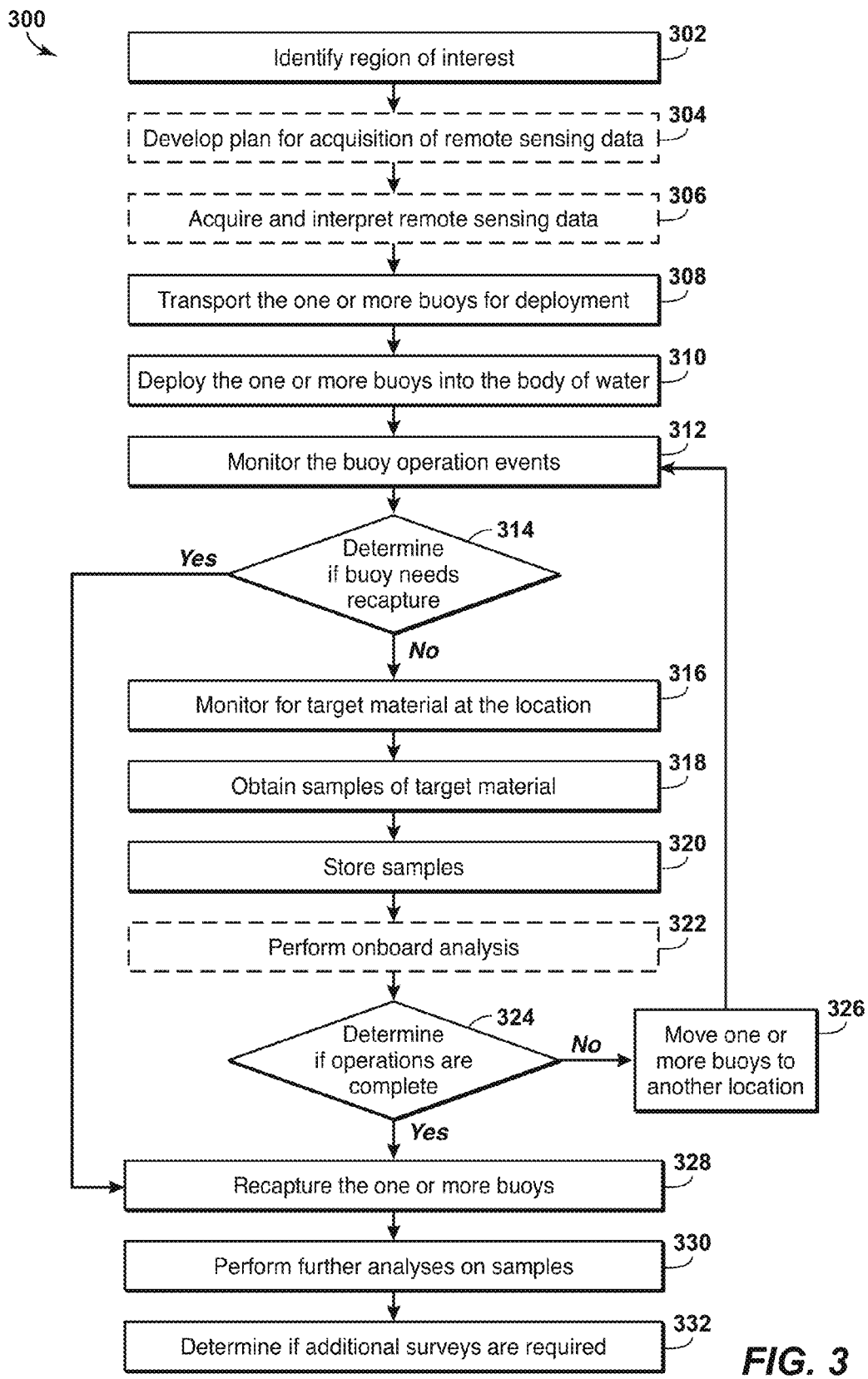
FIG. 3 is a flow chart for using remote sensing along with one or more buoy to perform marine surveying in accordance with an exemplary embodiment of the present techniques.

FIG. 3 is a flow chart 300 for using one or more buoys to perform marine surveying in accordance with an exemplary embodiment of the present techniques. In this flow chart 300, various blocks relate to identifying a region of interest, such as blocks 302 to 306, which may be referred to as the identification stage. Other blocks involve an operation and sampling stage, as shown in blocks 308 to 326. Finally, blocks 328 to 332 relate to further operations stage that may include collecting the buoy and may include further analysis of samples that may be useful for operations.

The identification stage is described in blocks 302 to 306. At block 302, a region of interest is identified. The identification of a region of interest (e.g., area of interest) may include performing various operations prior to deployment of the buoy via remote sensing. The remote sensing survey may include satellite imagery and airborne surveys. The remote sensing techniques may include synthetic aperture radar (SAR) images and/or other types of data that indicate the presence of target material. For example, the identification of a region of interest may include identification of a region of interest for study related to hydrocarbons, the biodiversity of the area, studying the water chemistry of a region of interest, identifying the extent of an algae bloom or other feature that may interrupt food supplies, fingerprinting a specific compound to determine its source or any other reason that sampling of fluids or sediments may be useful. The remote sensing data or information may be used to identify areas (e.g., regions of interest) that have a higher probability of being of useful for the survey. Then, additional data for the area of interest, such as wind direction and velocity for calculating potential movements over time, may be analyzed to further refine and verify the locations of interest. At block 304, a plan for acquisition of remote sensing data may optionally be developed. The plan for acquisition of remote sensing data may be developed before or during the buoy deployment (e.g., concurrently with buoy deployment). For example, the buoy deployment plan may be developed after reviewing any obtained data regarding the regions of interest. This may involve planning to acquire additional concurrent data for the area of interest, which may be prior to buoy deployment and continuing for the duration of the buoy deployment. At block 306, the remote sensing data may optionally be acquired and interpreted. The remote sensing data (e.g., SAR data) may be obtained prior to and/or concurrently with the buoy deployment operations (e.g., during buoy deployment). The remote sensing data may not need to be obtained if the region of interest is known or has been identified from other sources.

With the identified region or area of interest, the operation and sampling stage is performed in blocks 308 to 326. At block 308, the one or more buoys are transported for deployment. The buoys may be deployed via a deployment vessel. The deployment vessel may include a marine vessel or an airborne vessel that is capable of transporting the buoy to a location in or near the body of water. Prior to deployment into the body of water, the buoy is loaded with the appropriate sensors, sampling containers and other equipment that may be utilized for collection of different types of samples. Then, at block 310, the one or more buoys are deployed into the body of water. The deployment of the buoys may include preparing the buoys for operations and beginning the operations of the buoy. The deployment of the buoys may include programming the buoys to be configured to communication within the modules and components of the buoy, between modules and components of different buoys and/or the command unit. The deployment may also include placing one or more of the buoys into the body of water, moving the one or more buoys into the desired location, securing the one or more buoys at the desired location, and verifying the communication between the command unit with one or more of the components and/or modules associated with at least one of the buoys. The deployment may also include designing the configuration (e.g., geometry and layout plans for one or more buoys) for the region of interest. This determination may also include selecting communication configurations based on the configuration of buoys to manage the communication exchange between the modules and components that are part of the buoys and/or the command unit.

Once deployed, the operation of the buoys is monitored, as shown in blocks 312 and 314. At block 312, the buoy operation events may be monitored. The monitoring may include obtaining information (e.g., measurement data, status indicators or other signals that represent a buoy operation event). The one or more buoys may be configured to transmit information within a set time window (e.g., every 10 seconds, 60 seconds, 5 minutes, or even 10 minutes), transmit information when polled by the command unit, or transmit information when a buoy operation event occurs (e.g., the different modules indicate that the respective status has changed enough to indicate a buoy operation event has occurred). Then, at block 314, a determination is made whether to recapture the buoy. This determination may be made by receiving information from the one or more buoys and analyzing the information, as indicated above. This determination may be performed by the command unit executing a set of instructions on a computer system and providing an indication of the buoy operation event to an operator via a display and/or an audible signal. If no buoy operation event has occurred, then the process may continue to monitor for target material, as shown in block 316. However, if a buoy operation event has occurred that needs recapture, the buoy may be recaptured, as shown in block 326.

At block 316, the buoy may monitor for target material at the location. The target identification monitoring may involve confirming that the identified area of interest has the target material. The monitoring may include determining the types of samples to acquire, such as water, biological material, chemicals, hydrocarbons and/or other target materials (e.g., types may include obtaining information about aquatic organisms or hydrocarbons). As part of the monitoring, the buoy may utilize one or more modules of the measurement components (e.g., sensors) to identify the target material. For example, the sensors may include ultrasound measurements, analyzing the water to detect hydrocarbons, visible images to detect large mammals or schools of fish; and/or deploying an unmanned vehicle (e.g., a balloon or other airborne vehicle) above the buoy to obtain and analyze electromagnetic radiation data (e.g., infrared and visible light data) to identify the fauna, flora and/or waterborne hydrocarbons. The use of the unmanned vehicle (e.g., a balloon) may include deploying the unmanned vehicle above the buoy, wherein the unmanned vehicle has electromagnetic radiation module (e.g., infrared and visible light detection components); obtaining electromagnetic radiation images (e.g., infrared and visible light images) for the region around the buoy and analyzing the electromagnetic radiation images (e.g., infrared and visible light images) to identify flora, fauna and/or hydrocarbons.

At block 318, one or more samples of target material are obtained. The samples may be obtained by the buoy, which may include samples of water, sediment, hydrocarbons and/or other liquids. As may be appreciated, the operation of the buoy, which may be automated, may include various processes that repeat during the sampling stage or sample collection operations (e.g., period of time that the buoy is obtaining samples). For example, the buoy may utilize the one or more measurement components, such as one or more measurement modules, to communicate with the control unit, to manage the acquisition of the samples, to obtain samples, to calculate operational and sample parameters, to determine adjustments to the operation of the buoy and to determine if additional samples should be obtained. Also, the buoy may obtain samples, which are associated with aquatic organisms. Exemplary measurement components are described further below. Then, the samples may be stored in or on the buoy, as shown in block 320. The storage of the samples may include storing the samples in individual compartments, which are isolated from each other to lessen any cross contamination. The storing of the samples may involve managing the storage temperature of the samples (e.g., between about 10° C. and about −100° C.), which may be in the range between about −10° C. and about 10° C., for hydrocarbon samples and between about −10° C. and about −100° C., for biology samples. Exemplary techniques to store of the samples are described further below, which may involve the use of a storage component or module. At block 322, onboard analysis may optionally be performed. The onboard analysis may include analyzing one or more of the samples to verify the target material is present in the sample and/or analyzing one or more of the samples near the time of acquisition of the sample. The onboard analysis may be performed by one or more components on the buoy. Then, a determination is made whether the operations are complete, as shown in block 324. The determination may include obtaining a specific number of samples and/or obtaining certain types of samples. Alternatively, as the samples may include different information, the determination may include analyzing one or more of the samples on the buoy via respective modules or components to determine whether additional samples should be obtained. If the sample collection operations are not complete, the buoy may be moved to another potential location, as shown in block 326. The moving of the buoy may be performed by an unmanned vehicle (e.g., unmanned surface vehicle and/or unmanned airborne vehicle) or by the deployment vessel. The unmanned may retrieve the buoy via a hook and reel configuration, magnet or other suitable retrieval method.

However, if the sampling operations are complete, the further operations stage may be performed, as shown in blocks 328 to 332. At block 328, the buoy may be recaptured or redeployed to another potential location of interest. The recapture and redeployment of the buoy may include transmitting the location of the deployment vessel or unmanned surface vehicle. Then, at block 330, the obtained samples may optionally be further analyzed. The further analysis of the samples may include removing the samples from the buoy, providing the samples to a laboratory to perform the analysis, performing the analysis on a marine vessel that deploys the buoy, and/or obtaining results from the buoy after it performs the analysis and further processing the information. The analysis (which may be performed in a laboratory or onboard a deployment vessel) may include using a fluorometry, a gas chromatography (GC), mass spectrometry (MS) and/or other suitable GC-MS or GC-GC equipment. Also, the analysis may include DNA sequencing or additional techniques to obtain water chemistry, biodiversity assessments and other characterizations of the environment. In particular, the analysis may include determining the presence of particular species or chemical elements. The samples may be subjected to multiple independent analysis technologies, such as clumped isotope geochemistry, noble gas geochemistry, and microbiology. Each of the analysis may be utilized to provide additional information about the hydrocarbons, biological and/or chemical content of the environment. Then, in block 332, a determination is made whether additional surveying is needed. This determination may involve analyzing the data obtained from the further analysis, data obtained from the onboard analysis and/or operations in the area of interest. The additional surveying may involve biological surveying, chemical surveying and/or hydrocarbon surveying.

As an enhancement to the surveying, the sampling operations may lessen contamination of the samples by removing or inactivating live microbes from some of the obtained samples. The removal of microbes may involve exposing the sample to a compound that kills or inhibits the activity of microbes or degrading enzymes as it is being retrieved or once the sample is within the compartment. For example, the configuration may include a pump and nozzle disposed within each sampling container. Alternatively, sampling material may include a compound that kills or inhibits the activity of living microbes or degrading enzymes captured by the sampling material. Microbes may be inactivated by briefly subjecting the sample to temperature, salinity, or other physico-chemical treatments.

In addition, with the obtained samples, the buoy may also obtain other measurement data, such as camera images, temperature data, mass spectrometric data, conductivity data, fluorometric data, and/or polarization data, for example. The data can be in the format of images, raw data with specific format for the component, text files, and/or any combination of the different types. Other sensors may include functionality to provide chemical specificity of applied sensors (e.g., mass spectrometry). The measurements from these sensors may provide guidance on sampling strategy and location.

With the obtained samples and associated data, biodiversity may be modeled based on the analysis of the samples. The analysis of the samples may be integrated with other data to enhance or verify a model. As an example, the sample analysis data may be organized with the location of the buoy, and/or another location to correlate the sample analysis data with other measurements or models of the subsurface geology. That is, different types of data may be integrated based on location information associated with the respective data to enhance the characterization operations. For example, sample analysis data may be integrated with photographic images and/or sonic data in a region. Beneficially, the sample analysis data provides an enhancement in the marine surveying of bodies of water. In particular, the method may be utilized prior to drilling operations to establish a baseline for environmental conditions, such as biological and plant diversity as well as for water chemistry, for example. The environmental conditions may be collected over different periods of time (e.g., months, years and other suitable periods of time) and may be integrated with hydrocarbon data (e.g., hydrocarbon models, seismic data and/or other suitable hydrocarbon data) to provide an integrated perspective of the area of interest.

As yet another enhancement, the present techniques may involve the use of one or more buoys with an unmanned surface vehicle (USV) and/or unmanned airborne vehicle (UAV). For example, one or more sample containers may be acquired by a buoy at a potential location of target materials in the body of water. The buoy may drop, lower, launch or otherwise dispose one or more sample containers into the body of water. Once disposed in the body of water, the sampling container may contact the target materials. Then, the sampling container, which may include a sampling material, which has adhered (e.g., sorbed and/or adsorbed) target materials or an acquired fluid and/or sediment sample, is retrieved. In addition, a UAV and/or USV may be used to retrieve the samples or the buoy. The UAV and/or USV may then store the obtained samples, which may involve the storing of the samples by managing the temperature (with a suitable range for the given samples) within the sample containers on the UAV and/or USV. Then, the UAV and/or USV may be return to the deployment vessel or other suitable location for retrieval.

To locate the buoys for retrieval, the buoy may include locating components. That is, the buoy may include a locating beacon (e.g., an audible notification or other such communication equipment) and the unmanned vehicle may be configured to detect and navigate to the locating beacon. The unmanned vehicle may have a propulsion component, a communication component and/or a storage component. The propulsion component may be configured to maneuver the unmanned vehicle, the storage component may be configured to store the sample containers and the communication component may be configured to communicate signals associated with the operation of the unmanned vehicle. To manage the temperature of the samples, the storage component (e.g., a heating and/or cooling module or component) configured to maintain the temperature within the sampling container within a specified range. As an example, an unmanned vehicle having a propulsion component, a communication component, and a sample collection component may be used with one or more buoys to manage the deployment of the buoys and the samples collections from the buoys. The propulsion component may be configured to maneuver the unmanned vehicle, while the sample collection component may be configured to obtain one or more samples from the buoy, and the communication component may be configured to communicate with the buoy.

The sample containers may include various configurations. For example, the sample containers may include sample material or sample vessel, as noted above, along with a spool or may include other configurations to obtain samples, such as open tubes that seal at a certain depth or the like. Alternatively, the sample container may be a canister that has the sampling material sealed within the canister's housing. The sample container may include sensor or active component that is utilized to detect the presence of a target material. For example, the sample container may be configured to: maintain the sampling material sealed within the sample container if a particular target material (e.g., hydrocarbon, biological or chemical substance) is not detected; and unseal the sample container to provide interaction between the sampling material and the target material in a body of water when the target material is detected. As another example, the sample container may be configured to: maintain the sampling vessel sealed within the sample container if a particular target material (e.g., hydrocarbon, biological or chemical substance) is not detected; and unseal the sample container to provide interaction between the sampling vessel and the target material in a body of water when the target material is detected. Further, the sealing and unsealing operation may also be configured to be on a timer, remotely activated or any other suitable techniques. In particular, the sample container may be configured to seal the canister after a set period of time once the canister has been unsealed.

To collect samples, the buoy may include various sampling containers. For example, obtaining of the samples may be performed with the buoy having an assembly including 50 to 100 individual sampling containers. Each sample container includes sampling material or sampling vessel that is deployed from the sample container and then retrieved back into the sample container. For the sampling material configuration, the target materials are contacted with the sampling material adhere to the material, and then the sampling device is retrieved back into the sampling container. The sampling material may be TFE-fluorocarbon polymer screening fabric and may have a thickness of about 0.1 millimeters (mm) to 0.7 mm, or more preferably about 0.3 mm. The sampling container is sealed and temperature-controlled for the duration of the buoy deployment. Other sample containers may be lowered to a specific depth, opened, filled, and sealed. These containers may also be maintained in a temperature controlled environment.

Figure 4A:
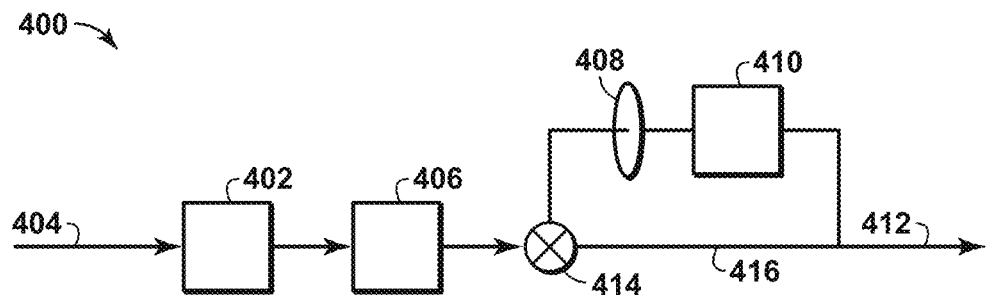
FIGS. 4A to 4E are diagrams for exemplary sampling modules in accordance with an exemplary embodiment of the present techniques.

FIGS. 4A to 4E are diagrams 400, 430, 440, 450 and 460 for exemplary sampling modules in accordance with an exemplary embodiment of the present techniques. In FIG. 4A, a diagram 400 of a detection and sampling module may include a pump 402 coupled to an inlet conduit 404, a target measurement device 406 (e.g., fluorometer or mass spectrometer), a filter 408, valve 414, bypass conduit 416 and a solid phase extraction (SPE) module 410, which is coupled to a discharge conduit 412. In this configuration, a pump 402 draws target material (e.g., water and waterborne liquid hydrocarbons) from the body of water. The pump 402 is used to actively move the fluids, which may include liquids, gases and/or solids, from the body of water through the inlet conduit 404 into the target measurement device 406. The fluid is analyzed in the target measurement device 406 to determine if the target material (e.g., hydrocarbons) is present. The fluid is normally directed by the valve 414 to flow directly to the discharge conduit 412 through the bypass conduit 416. If the target measurement device 406 indicates that the fluid contains or buoy is in contact with target material (e.g. waterborne hydrocarbons), then the valve 414 directs at least a portion of the fluid through filter 408, which includes filter media, and the SPE module 410 for a period of time. The SPE module 410 may be a cartridge that is placed into a sample container to isolate the sample from other samples. Solid in the fluids along with target materials (e.g., hydrocarbons) may be adsorbed or captured by the filter media and target material in the fluid may be adsorbed onto the SPE material, while the remaining fluid continues on to the discharge conduit 412. The remaining portion of the fluid at the valve 414 is passed through the bypass conduit 416 to the discharge conduit 412. The portions are combined and passed through the discharge conduit 412. After the sample collection period, the valve 414 is adjusted back to the position that directs the flow of fluids to the discharge conduit 412 through the bypass conduit 416. The used filter and SPE module (e.g., SPE cartridge) may be removed from the bypass conduit 416 and an unused assembly may be inserted to replace the used filter 408 and SPE module 410. Beneficially, this configuration does not involve deployment or retrieval of sampling material. The described module has strong synergies with a buoy equipped with a flow-through fluorometer for the purpose of indicating the presence or waterborne liquid hydrocarbons.

Further, in other embodiments, other mechanisms may be used to detect the presence of target material. In such embodiments, the valve 414 may be controlled by signals from the target material detection module. Alternatively, the system may include periodic activation. For example, the valve 414 may be periodically positioned to provide fluid from the body of water to flow through the filter 408 and SPE module 410 to collect one or more samples.

Figure 4B:
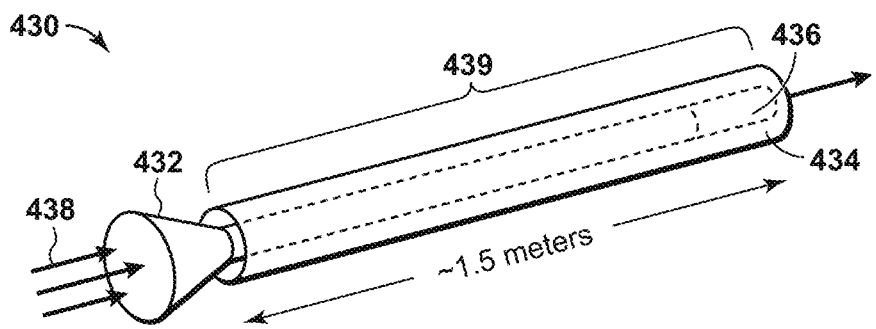

In FIG. 4B, a diagram 430 of sampling module may include a flow diverter 432 coupled to a sampling conduit 434 with a sampling material 436. In this configuration, a fluid is passed through the flow diverter 432 into the sampling conduit 434 to interact with the sampling material. Then, the flow of fluids may be interrupted and the sampling conduit 434 having the sampling material 436 may be removed from operations and stored as a sample. The sampling conduit may be sealed at both ends and/or placed into a sampling container for storage to isolate the sample.

Beneficially, this configuration, integrates a larger volume of water to accumulate target materials (e.g., hydrocarbons) to useable levels. The sampling module is a flow-tube accumulator, which may be a passive configuration that can be integrated with other detection systems to unseal the access to the sampling material. Being a passive configuration, the movement of the tide and current may move the fluid through the sampling material, as shown along arrows 438. This configuration lessens power consumption, while providing an enhanced technique for collecting samples. Further, the proposed flow-tube accumulator is configured to extract (e.g., integrate) hydrocarbon droplets as large quantities of fluid are drawn through the sampling conduit 434.

Several configuration considerations may be considered for this sample module. For example, the platform may be attached to a variety of devices, such as the buoys noted above. In a shallow-water environment, the sampling module may be attached to a tow body or otherwise pulled through the body of water. In certain applications, the drag on the sampling module is a lesser concern because the tow body has considerable drag. In deep water applications, the sampling module may be towed behind or incorporated within an AUV or other submerged vessel. In other applications, power considerations may dictate lessening flow-related drag and may lead to different design choices (e.g., a smaller tube). Another possible platform may be more stationary, such as a buoy, where volumes of water are pulled through the sampling conduit 434 passively and/or using a pump to extract from volumes of water from a specific location.

In another configuration consideration may include different tube structures for the sampling conduit 434 (e.g., funnel; geometric parameters (length, diameter); active versus protected zones). For example, the tube geometry may be adjusted. Parameters to optimize include the tube length 439 and diameter and the possible collecting funnel at the intake. Flow simulation considering these parameters (and the sampling geometry discussed below) may be used to maximize the capture and retention of colloidal hydrocarbon droplets. An optimal flow rate related to these geometric parameters may maximize the capture of droplets over a large filter surface area, while minimizing the stripping out of previously captured sample.

Figure 4C:
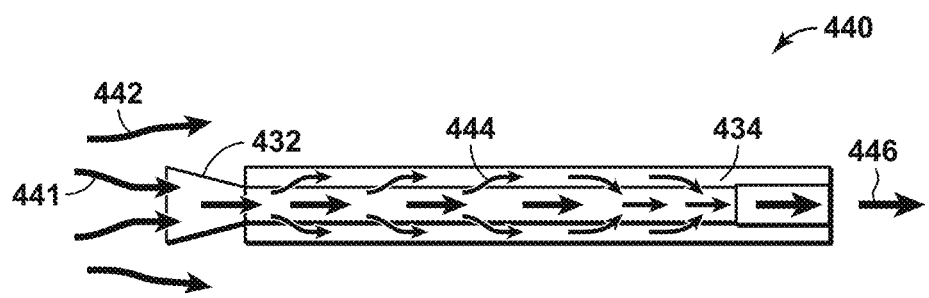

The flow modeling, as shown in FIG. 4C, is a diagram 440 showing the flow of fluids through the sampling conduit 434. This diagram 440 highlights issues like net drag, pressure build up at the intake that diverts flow, parallel paths through the collecting area, and possible turbulent and quiescent regions. In particular, the flow passage represented by arrows 441 enter the sampling conduit 434, while the flow passages represented by arrows 442 bypass the sampling conduit 434. Further, the flow passage as represented by arrows 444 is within the sampling conduit 434, while the flow passages as represented by arrows 446 are exiting the sampling conduit 434.

Figure 4D:
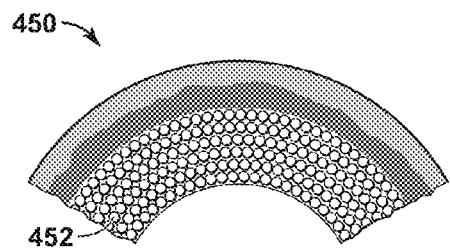
Figure 4E:
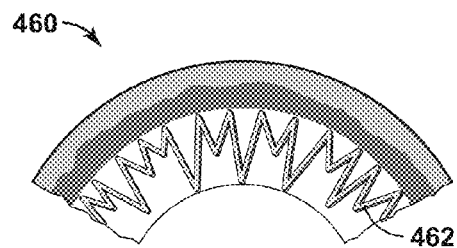

In yet another embodiment, the sampling material may be adjusted for geometry and chemistry. The sampling material geometry may include an annular collecting zone surrounding the central flow channel. A large effective collecting surface with many parallel paths may be desirable to maximize capture with minimal net drag. The sampling geometry may include bead pack; pleated-folded sheet; mesh; sponge; wool; and/or fiber rope. As an example, FIG. 4D is a diagram 450 of a bead pack 452, while FIG. 4E is a diagram of a folded sheet 462. Further, the sampling material chemistry may include a material lining in the sampling conduit (e.g., collecting tube portion) may include one or more materials. These materials may include Teflon sheets or mesh, copper (Cu) or alloys (e.g., bronze wool and/or an antimicrobial), polydimethylsiloxane (PDMS), or silicone paste. Materials may also be coated (e.g., with C18 as in SPE tubes). The sampling material properties may be incorporated into the flow modeling, which may be modeled at different scales to understand local versus large-scale effects.

Figure 5:
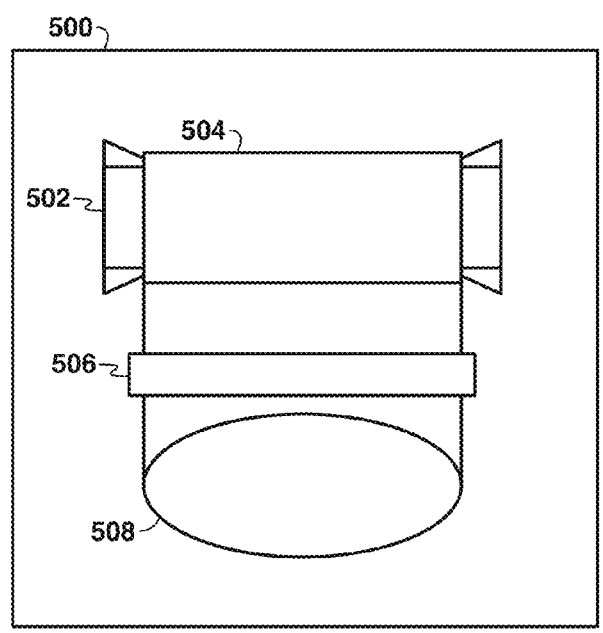
FIG. 5 is a diagram of an exemplary sample container in accordance with an exemplary embodiment of the present techniques.

FIG. 5 is a diagram of an exemplary sample container 500 in accordance with an exemplary embodiment of the present techniques. In this sample container 500, sampling material 504 may be disposed around a spool 502. The sampling material 504 may be attached to the spool 502 at one end, while the other end of the sampling material 504 may be attached to a buoyant weight 508. The buoyant weight 508 may be configured to float on the body of water to maintain the sampling material 504 in contact with the surface of the body of water, may be configured to sink within the body of water to maintain the sampling material 504 at a specific target depth and/or may be configured to contact the sediments at the bottom of the body of water. To control the distribution of sampling material 504, a guide member 506 may be disposed between the spool 502 and the buoyant weight 508. The spool 502 may dispense and retrieve the sampling material 504 through the use of a motor and/or other mechanism (not shown). Beneficially, by having the sampling material 504 in an individual sample container, cross contamination from different samples may be lessened.

As an example, the sampling material 504 may be deployed on a spool 502 that is about 12 centimeters (cm) wide. If the configuration includes 50 to 100 individual sampling containers, each of the individual sampling containers contains one such spool 502. The spool 502 is actuated to activate the deployment and retrieval of the sampling strip of the sampling material 504. The end of the strip is weighted, such as the buoyant weight 508, so that tension exists on the strip to ensure proper deployment down to the desired location (e.g., preventing the strip from being lifted and flapping due to wind) and proper spooling upon retrieval (e.g., slack in the line hinders smooth retrieval). The weight on the end of the strip is buoyant, so that it does not cause the strip to sink below the surface of the body of water or it does not cause the strip to sink below the preferred depth. A metal guide-piece, such as guide member 506, is also in place below the spool to aid in proper spooling and to avoid snagging of the strip on the opening of the sampling container during retrieval. The guide member may have rounded edges to lessen scraping the target material off of the sampling material during retrieval. The guide member may also be configured from two rollers. The guide member also prevents twisting during spooling. The buoyant weight 508 may be configured to not pass through the guide member to provide a stopping mechanism for the spooling mechanism.

The sample container 500 may also include other configurations that may be combined with the sampling material configuration. For example, a sampling vessel, which may replace the sampling material 504, may be coupled to the spool 502 to acquire fluid samples. The sampling vessel may be attached to the spool 502 at one end, while the other end of the sampling vessel may be attached to a buoyant weight 508. Similar to the sampling material configuration, the buoyant weight 508 may be configured to float on the body of water to maintain the sampling vessel in contact with the surface of the body of water, may be configured to sink within the body of water to maintain the sampling material 504 at a specific target depth and/or may be configured to contact the sediments at the bottom of the body of water. Beneficially, the sampling vessel may be placed individually within a sample container to lessen cross contamination from different samples.

In yet another example, an imaging module may replace the sampling material 504 and may be coupled to the spool 502 to acquire images of portions of the body of water. The imaging module may be attached to the spool 502 at one end, while the other end of the imaging module may be attached to a buoyant weight 508. Similar to the sampling material and sampling vessel configuration, the buoyant weight 508 may be configured to float on the body of water to maintain the imaging module in contact with the surface of the body of water and/or may be configured to sink within the body of water to maintain the sampling material 504 at a specific target depth. Beneficially, the imaging module may store images on the buoy or may store the imaging module individually within a sample container.

As may be appreciated, the sampling container may involve different configurations. For example, the sampling container may be a rectangular prism to maximize the packing density of the containers and thus the quantity of samples onboard for a given space. These sampling containers may include various different types of target materials in the individual sampling containers. The bottom surface may be a swinging door that is opened and closed using an electric motor that is housed outside of the sample container. Actuators may be disposed outside of the sample container to avoid contamination issues caused by lubricant oil, etc. The door may swing open using a hinge at one end of the sample container, such that the sample material may exit the sample container using gravity. The door orientation may be configured to prevent the door from interfering with the sample material as it is deployed and retrieved (e.g., positioned at the end of the sampling container that is near the front of the buoy. When the door is opened, it should open as wide as possible, so as to avoid contacting or interfering with the sample material, sampling vessel or other sampling module. The hinge should be configured to lessen it as a source of sample contamination, so the materials and lubrication should be carefully considered. The door should make a tight seal when it is closed to isolate the sample material, sample vessel or other sampling module and oil sample from the environment. The doors may be firmly sealed even in extreme sea states where they are being rapidly accelerated and decelerated and being struck by waves. The seal may preferably be air and water tight. The door may also include a thermally insulating layer to reduce heat loss to the environment. The motor should be IP66 certified, which certifies that the device is dust tight and can prevent water ingress even while being washed down under high pressure. The rugged operating environment makes this necessary. The door and motor drive described are shown in FIGS. 6 and 7.

Figure 6:
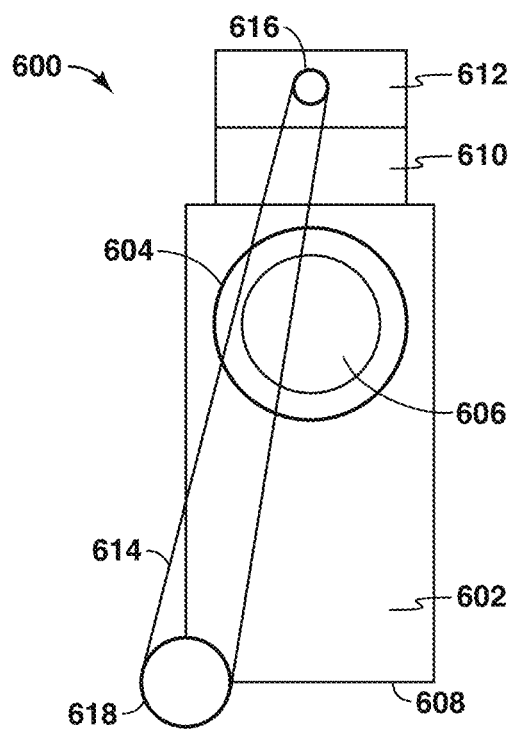
FIG. 6 is a diagram of an exemplary sample container having a motor drive in accordance with an exemplary embodiment of the present techniques.

FIG. 6 is a diagram of an exemplary sample container configuration 600 having a motor drive for the door in accordance with an exemplary embodiment of the present techniques. In this configuration 600, the sample container 602 may include a sampling material 604 may be disposed around a spool 606. Similar to the discussion of FIG. 5, the sampling material 604 may be attached to the spool 606 and use buoyant weight and guide member (not shown). In this configuration 600, a door 608 is disposed at the end of the sampling container adjacent to the body of water. The configuration 600 includes a first electric motor 610 that may be used to operate the spool 606 and a second electric motor 612 that is utilized to open and close the door 608. The first electric motor 610 is utilized to operate the spool 606 to deploy and retrieve the sampling material 604. The second electric motor 612 is utilized to open and close the door 608, which may utilize a belt or chain 614 and pulleys 616 and 618. As may be appreciated, other configurations may include a sample vessel or other sampling module instead of the sampling material.

Figure 7:
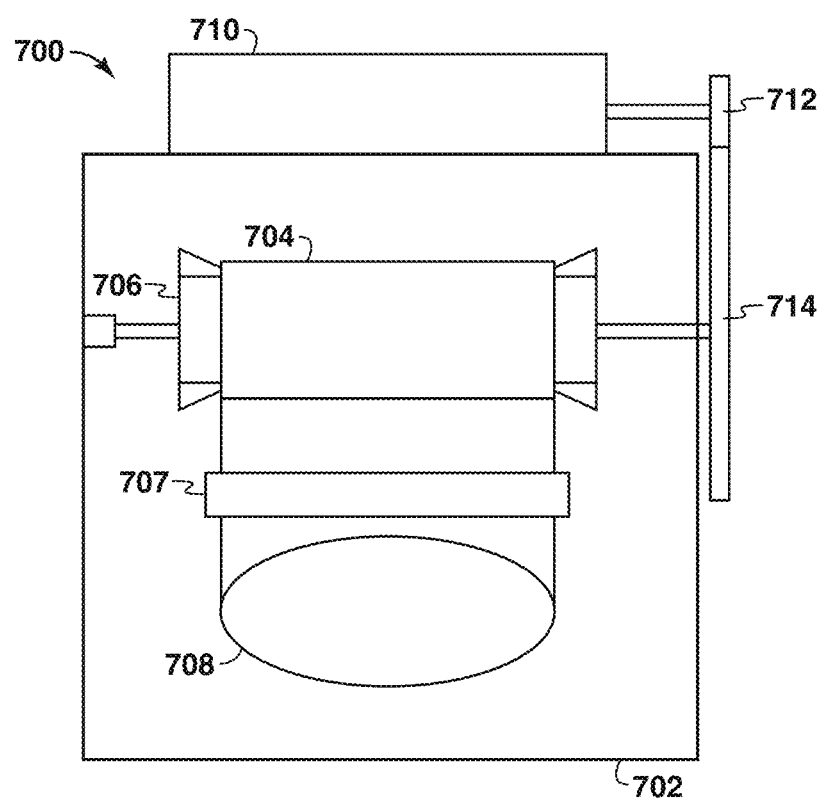
FIG. 7 is a diagram of an exemplary sample container configuration having a motor drive for the spool in accordance with an exemplary embodiment of the present techniques.

FIG. 7 is a diagram of an exemplary sample container configuration 700 having a motor drive 710 or the spool 706 in accordance with an exemplary embodiment of the present techniques. In this configuration 700, the sample container 702 may include a sampling material 704 may be disposed around a spool 706. Similar to the discussion of FIGS. 5 and 6, the sampling material 704 may be attached to the spool 706 and use buoyant weight 708 and guide member 707. The electric motor 710 may be used to deploy and retrieve the sampling material 704 from the spool 706. The electric motor 710 is configured to engage with a shaft and a first gear 712, which is configured to engage with the second gear 714. The second gear 714 may be configured to engage with a shaft that coupled to the spool 706.

Through this coupling, the electric motor 710 deploys and retrieves the sampling material 704. The spool 706 may be rotated by the electric motor 710 to deploy and retrieve the sampling strip of sampling material 704. The actuator may be placed outside of the container to avoid contamination, and may be placed on top of the sampling container 702 to reduce the footprint of the sample container 702. The rotational motion may be transmitted to the spool axle via gears 712 and 714 on the outside of the sample container 702. The electric motor 710 and gears 712 and 714 may or may not need to have additional housing around them. The other end of the spool axle may be seated in a bearing hole to provide free rotation, while holding the axle in place. The motor 710 may be dust tight and can prevent water ingress even while being washed down under high pressure (e.g., IP66 certified). In this configuration 700, the sample container's opening through which the spool axle extends may also be sealed. That is, it should be an airtight and watertight seal to avoid any contamination. Additionally, the sealing material 704 may be considered as it could be a source of sample contamination. While it may be preferred to not use any lubrication for the spool axle (as shown in FIG. 7), it should be configured to lessen any sample contamination from the lubrication. As may be appreciated, other configurations may include a sample vessel or other sampling module instead of the sampling material.

To enhance the operations, the spool may be configured to easily install and remove from the sample container. That is, the sample containers may be configured to provide easy removal and insertion for shipment to the lab. Accordingly, the configuration may include a design that provides a spool gear that is easy to remove (e.g., with a pin or nut securing the gear into the system). After the gear is removed, then the spool axle may be pulled out of the sample container, which results in the spool being free to drop out of the sampling container. A new spool may then installed by placing it into the container, sliding the axle, which may be keyed, through the spool, and securing the gear back on to lock the spool in place. As an example, the sampling container may be approximately 16 cm in width, 4 cm in depth, and 11 cm in height with an additional 5 cm of height below the container to accommodate the swinging door.

Figure 8:
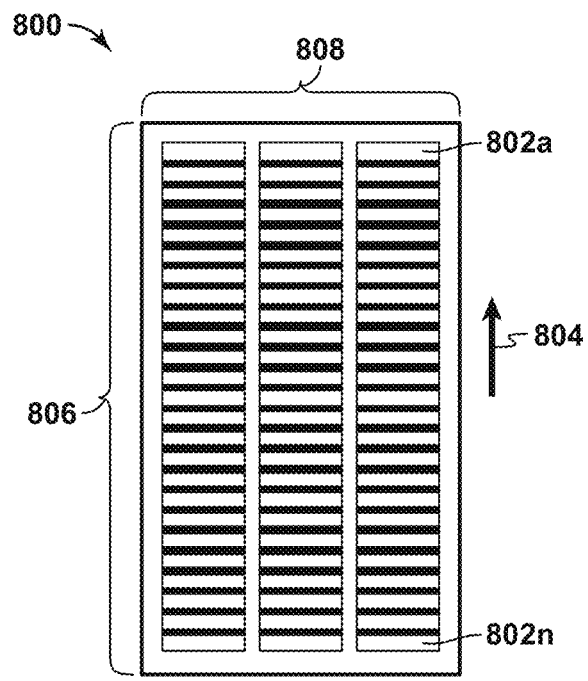
FIG. 8 is a diagram of an exemplary sample assembly having multiple sample containers in accordance with an exemplary embodiment of the present techniques.

The sample containers may be arranged into different configurations and may include different types of samples. For example, the sampling containers may be arranged and mounted within the sampling assembly, as shown below in FIG. 8. FIG. 8 is a diagram of an exemplary sample assembly 800 having multiple sample containers 802a to 802n in accordance with an exemplary embodiment of the present techniques. In this configuration 800, the sample assembly may be a rectangular prism that includes from 50 to 100 sampling containers 802a to 802n, which are also rectangular prisms. The sampling assembly may have a height 806, a width 808 and depth (not shown), which provide the dimensions of the rectangular prism. As an example, the sampling assembly 800 may be approximately 0.6 meters (m) in width, 11 cm in depth, and 1 m in height. This sampling assembly of such dimensions may include 75 sampling devices. The diagram is a view of the doors for the sampling containers 802a to 802n, which may have one or more electric motors to open and close the doors and deploy and retrieve the sampling material from within the individual sampling containers 802a to 802n. The sampling assembly may include additional space above for the motor and other components (e.g., which may be housed inside an enclosure) and have an additional space of about 5 cm of height below the container to accommodate the swinging door for the sampling containers 802a to 802n.

The actual size of the sampling assembly depends largely upon the buoy platform. In the sampling assembly, a gap around each sampling container (e.g., between 2 cm to 4 cm or about 3 cm) except where the containers are adjacent and connected to each other in the fore-aft direction. The fore and aft walls of the sample containers may be a shared piece of metal plate. The 3 cm gap may be utilized to accommodate the gear and belt drives on either side of the sampling containers and also to provide mechanism to flow a cooling fluid between the sampling containers. The temperature control components are explained further below.

In other configurations, the different types of samples may be stored in different portions of the buoy. For example, hydrocarbon samples may be stored in a first portion that is managed at a first temperature, while biological samples are stored in a second portion that is managed at a second temperature. Further, the chemical samples may be stored with the hydrocarbon samples or may be stored in a third portion that is managed at a third temperature.

Figure 9:
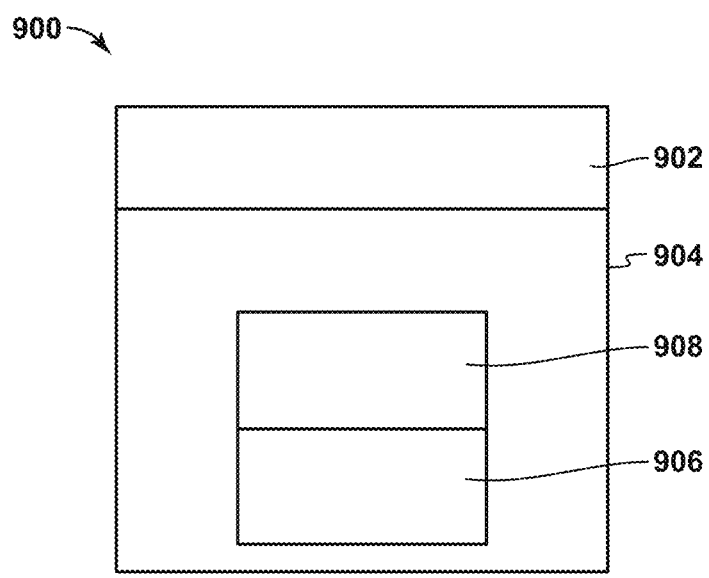
FIG. 9 is a diagram of an exemplary buoy in accordance with an exemplary embodiment of the present techniques.

To collect samples, the sampling assembly may be disposed on a buoy, as shown in FIG. 9. FIG. 9 is a diagram of an exemplary buoy 900 in accordance with an exemplary embodiment of the present techniques. In this diagram, the sampling assembly 906 is disposed on a buoy 904, which includes various components 902, which may be utilized for communication, sampling, detection and/or identification, power distribution and/or propulsion along with managing autonomous operations, if necessary. The sampling assembly 906 may include various individual sample containers that are used to obtain samples (e.g., deploy the sampling material onto the surface of the body of water). For example, the sampling material, which may be a strip, is sized so that approximately 1 m of the sampling material is in contact with the water's surface during sampling. The strip is then dragged through the target materials based on the sampling pattern before being retrieved back into the sampling container, which is subsequently sealed shut. For other configurations, the sampling material is sized so that approximately 1 m of the sampling material is in contact with the body of water at the desired depth during sampling.

Further still, the materials of construction of the buoy and sampling assembly are evaluated to consider any possible contamination effects they may have on the obtained samples. Adequate freeboard may be preferred, so that the sampling material is not lifted by waves into the bottom surface of the sampling assembly during sampling operations. The configuration of the buoy may be such that sampling may occur without the sampling material coming in contact with any part of the vessel.

Further, the buoy 900 may also include heating and cooling or storage component 908 configured to maintain the temperature of the samples within a specified range. For example, the sample temperatures for hydrocarbon samples should be maintained above $-10°$ C. (e.g., for hydrocarbons this prevents irreversible crystallization of waxes). Samples for microbial ecology may be preserved at temperatures lower than $-10°$ C., such as in a Dewar of liquid nitrogen. As an example, the temperatures for biological samples may be between about $-10°$ C. and about $-100°$ C. or between about $-20°$ C. and about $-100°$ C. Further, if the sample temperatures are too high, bacteria may degrade the sample. Accordingly, storage component 908 may maintain the samples at temperatures between about $-10°$ C. and $10°$ C., temperatures between about $-5°$ C. and $10°$ C., and/or temperatures between about $4°$ C. and $5°$ C., which may be specified in ASTM D4489-95.

The cooling and heating or storage components 908 may include various modules to operate. For example, the storage components 908 may include a mobile temperature management unit that maintains a heat transfer fluid. Exemplary mobile temperature management units are commercially available and utilized for the transport and temperature control of biological samples. In this configuration, the heat transfer fluid should be configured to not freeze or vaporize in expected temperatures that the buoy may be exposed to during operations. The heat transfer fluid should also be compatible with the materials with which it is in contact. The temperature of the heat transfer fluid is controlled inside of the mobile temperature management unit, and it is circulated inside of the sampling assembly to heat or cool the sample containers, keeping their temperatures in the acceptable range.

Figure 10:
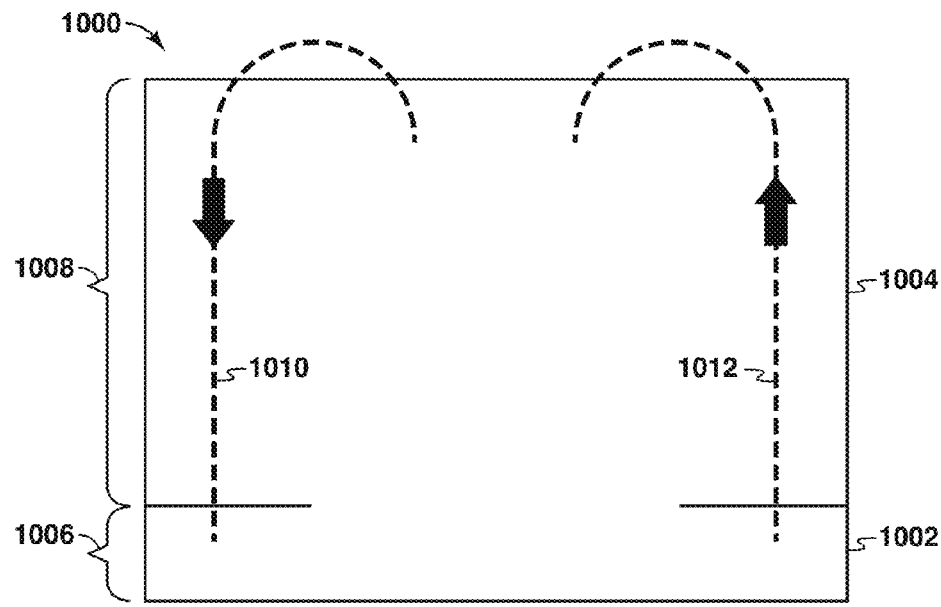
FIG. 10 is a diagram of an exemplary sample assembly and storage component in accordance with an exemplary embodiment of the present techniques.

As an example, FIG. 10 is a diagram 1000 of an exemplary sample assembly 1002 and storage component 1004 in accordance with an exemplary embodiment of the present techniques. In this diagram 1000, the sampling assembly 1002 is disposed below (e.g., closer to the body of water than) the storage component 1004. The storage component 1004 may include various conduits, temperature control sensors, heat transfer fluid and pumps that are utilized to maintain the sample containers within the sample assembly 1002 within a predetermined temperature range. As an example, the sampling assembly 1002 may have a depth 1006 of 0.15 m, while the storage component 1004 may have a depth 1008 of 0.6 m. The length and width may vary, but may be similar to the sampling assembly. As noted above for the sampling assembly example, the storage component 1004 may have a length that is 1 m and the width is 0.6 m, which may be disposed over the sampling assembly.

To maintain the temperature, the heat transfer fluid may be circulated, as shown by arrows 1010 and 1012, using a small pump located inside of the storage component 1004 or elsewhere. For cold environments, the heat transfer fluid may be a water-based fluid combined with an anti-freeze agent to prevent ice from forming. For warmer environments, the heat transfer fluid may include water and/or seawater. Other fluids and additives are also considered and combined with the heat transfer fluid, as may be appreciated. The heat transfer fluid does not have to completely fill the areas of the sampling assembly outside of the individual sampling containers. That is, an air gap may be provided in the top portion of the sampling assembly, so that any electric motors are not submerged. Further, the sampling assembly may be compartmentalized to contain the heat transfer fluid below a certain level to reduce the amount of contact with the electric motors.

To manage the temperature, one or more thermocouples may be disposed in each sample container or adjacent to the sample containers to monitor the sample temperatures. This information may be stored (e.g., logged) and/or communicated to a control unit that may adjust the temperature by changing setting in the storage component 1004.

To provide quality assurance, a camera may be utilized to capture different aspects about the operations. That is, the camera may record interesting time segments of sampling operations in video or snapshot form and/or may be used to obtain images associated with aquatic organisms. The camera may specifically record the deployment and/or sampling operations for each sample. Further, the camera may be utilized to capture biological data, as well.

In one or more configurations, the samples may be processed on the buoy via measurement components. Alternatively, the samples may be transported to another location for analysis. The analyses may include chemical and isotopic analysis (e.g. mass spectrometry and/or fluorometry and/or analysis for noble gases and isotopologues), sediment analysis, biological analysis (e.g. DNA analysis), and/or other methods. See, e.g., Chase, C. R., Lyra, G., & Green, M. (2010, October). Real-Time Monitoring of Oil Using Ultraviolet Filter Fluorometry. Sea Technology.

Data from the sensors onboard the buoy may be communicated back to operators via communication equipment (e.g., Iridium satellite) and stored and analyzed in a database, while the buoy is deployed. Commands may be sent to the buoy from the shore or from a manned vessel. While the communications may be based on a variety of technologies, the buoy may use an Iridium satellite link to provide the primary means for communicating navigation and sensor measurements to the remote operator. The same system may also be used as the primary means of relaying commands to the vehicle. When higher bandwidth is required, perhaps during sampling activities, the RUDICS satellite communication system may be used, for example.

In additional embodiments, the sensors include a target detection modules (e.g., buoy-fluorometer(s)) to screen the screen potential target materials for possible anthropogenic contamination (e.g., diesel fuel) or other substances that indicate that the target materials are not sample contamination. Additionally, these sensors within a buoy can be used to map chemical or physical anomalies around target materials to locate the potential discharge locations. The analysis of the target materials may provide information based on biological and chemical sampling of fluids, gases, and sediments In one or more embodiments, the buoy may include other components to perform the operations. For example, the buoy may include a housing that encloses one or more of a communication component and associated antenna, a sample component, another measurement component, a power component and a propulsion component on one or multiple buoys. The modules and components may be provided power from the power component via power distribution lines (not shown). Similarly, the different modules and components may communicate with each other via communication lines. The central power and communication lines may be enclosed to be isolated from the environment and to manage the operation in an efficient manner.

To operate, the power component may be utilized to supply power to the various components. For example, the power component may provide power to the communication component and the other measurement components and temperature regulation components. The power component may include a battery, motor and/or solar powered equipment. The batteries may provide power via the power distribution lines, which may include one or more cables, as an example. The motor may turn fuel into power, which may be used to power the modules and components and also to recharge the batteries.

The communication component may be utilized to exchange information between the different modules and components and/or the command unit via the communication lines and the communication antenna. The communication component may utilize the communication lines to handle the exchange of information, such as measured data, status indications or other notifications between the modules, such as the sample component, the other measurement components, the power component and the propulsion component. The communication lines may include a bus, Ethernet cable, fiber optics or other suitable physical connection. In an alternative embodiment, the communication between modules may be via a wireless connection. Similarly, the communication protocol may be any protocol known to those skilled in the art. The communication components may include communication equipment that is utilized to communicate with one or more of other buoys, marine vessels and/or command units. The communication equipment may utilize technologies, such as radio, cellular, wireless, microwave or satellite communication hardware and software.

To sample and measure the target materials, the sample component may be utilized to measure various features of the target materials. Examples of different measurement components and the associated techniques to obtain measurements are noted further above.

In other embodiments, the present techniques provide an enhanced marine surveying method that obtains information for biodiversity at different trophic levels, such as environmental deoxyribonucleic acid (eDNA) (e.g., environmental assessment and monitoring). The present techniques may provide useful information on various environmental features, including biodiversity, chemistry, and ambient physical properties.

Persons skilled in the technical field will readily recognize that in practical applications of the disclosed methodology, it is partially performed on a computer, typically a suitably programmed digital computer. Further, some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing" or "computing", "calculating", "comparing", "determining", "displaying", "copying," "producing," "storing," "adding," "applying," "executing," "maintaining," "updating," "creating," "constructing" "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present techniques also relate to an apparatus for performing the operations herein. This apparatus may be specially constructed for the required purposes, or it may comprise a general-purpose computer selectively activated or reconfigured by a computer program stored in the computer (e.g., one or more sets of instructions). Such a computer program may be stored in a computer readable medium. A computer-readable medium includes any mechanism for storing or transmitting information in a form readable by a machine (e.g., a computer). For example, but not limited to, a computer-readable (e.g., machine-readable) medium includes a machine (e.g., a computer) readable storage medium (e.g., read only memory ("ROM"), random access memory ("RAM"), magnetic disk storage media, optical storage media, flash memory devices, etc.), and a machine (e.g., computer) readable transmission medium (electrical, optical, acoustical or other form of propagated signals (e.g., carrier waves, infrared signals, digital signals, etc.)).

Furthermore, as will be apparent to one of ordinary skill in the relevant art, the modules, features, attributes, methodologies, and other aspects of the invention can be implemented as software, hardware, firmware or any combination of the three. Of course, wherever a component of the present invention is implemented as software, the component can be implemented as a standalone program, as part of a larger program, as a plurality of separate programs, as a statically or dynamically linked library, as a kernel loadable module, as a device driver, and/or in every and any other way known now or in the future to those of skill in the art of computer programming Additionally, the present invention is in no way limited to implementation in any specific operating system or environment.

Further, one or more embodiments may include methods that are performed by executing one or more sets of instructions to perform modeling enhancements in various stages. For example, the method may include executing one or more sets of instructions to perform comparisons between thresholds current statuses or indications along with transmitting data between modules, components and/or sensors.

As an example, a computer system may be utilized and configured to implement on or more of the present aspects. The computer system may include a processor; memory in communication with the processor; and a set of instructions stored on the memory and accessible by the processor, wherein the set of instructions, when executed, are configured to: receive a transmitted signal from the buoy; determine whether the transmitted signal indicates that a buoy operation event has occurred; provide one or more of a visual indication and audible notification associated with the buoy operation event, if a buoy operation event has occurred; and store the updated status in memory if a buoy operation event has not occurred. Further, the determination of whether the transmitted signal indicates that the buoy operation event has occurred may include a set of instructions, when executed, configured to: compare current buoy location to an initial buoy location; and compare the difference between the locations with a threshold; if the difference greater than the threshold, then indicate that a buoy operation event has occurred; and if the difference is less than or equal to the threshold, then indicate that a buoy operation event has not occurred. These initial locations may be stored in memory or transmitted from the buoy. Also, the determination of whether the transmitted signal indicates that the buoy operation event has occurred may include a set of instructions, when executed, configured to: compare the measured resistance to a resistance range; and if the measured resistance is within the resistance range, then indicate that a buoy operation event has occurred; and if the measured resistance is outside the resistance range, then indicate that a buoy operation event has not occurred. The resistance range may be a predetermined range for hydrocarbons resistance, and/or may include a range that indicates that the circuit has been disconnected (e.g., indicating that the skirt section has been damaged). Further still, the determination of whether the transmitted signal indicates that the buoy operation event has occurred may include a set of instructions, when executed, configured to: compare the measured pressure to a pressure range of hydrocarbon resistance; and if the measured pressure is within the pressure range, then indicate that a buoy operation event has occurred; and if the measured pressure is outside the pressure range, then indicate that a buoy operation event has not occurred. The pressure range may be the preferred operational pressure range for the flotation section and/or the pressure range may indicate that water is present at the sensor location.

Figure 11:
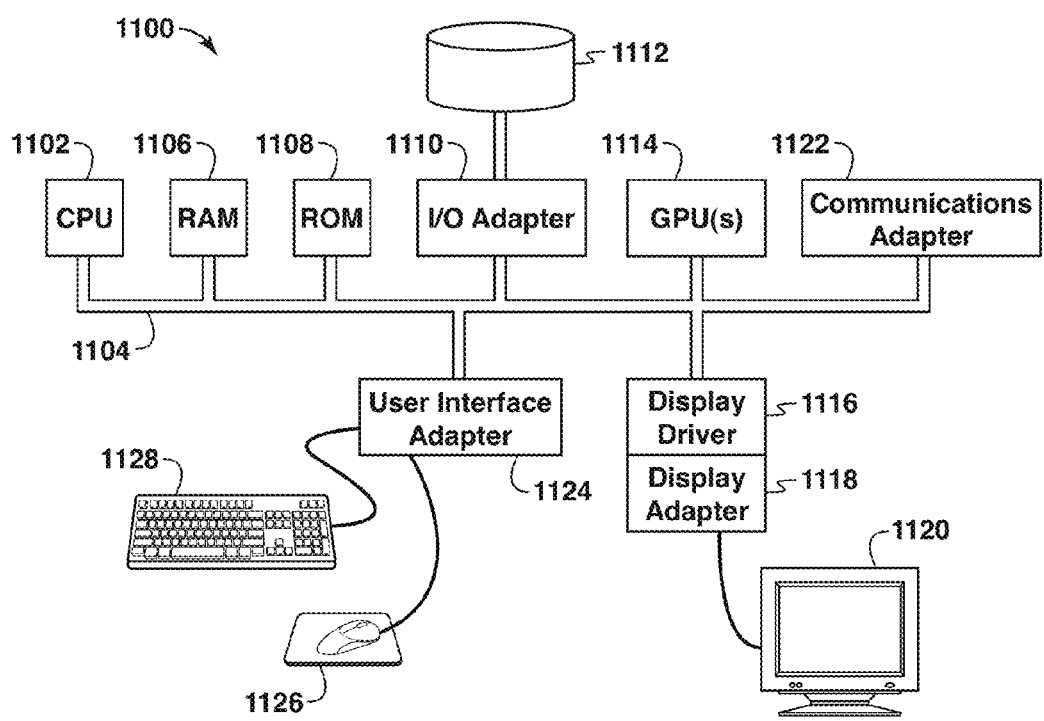
FIG. 11 is a block diagram of a computer system that may be used to perform any of the methods disclosed herein.

As an example, FIG. 11 is a block diagram of a computer system 1100 that may be used to perform any of the methods disclosed herein. A central processing unit (CPU) 1102 is coupled to system bus 1104. The CPU 1102 may be any general-purpose CPU, although other types of architectures of CPU 1102 (or other components of exemplary system 1100) may be used as long as CPU 1102 (and other components of system 1100) supports the inventive operations as described herein. The CPU 1102 may execute the various logical instructions according to disclosed aspects and methodologies. For example, the CPU 1102 may execute machine-level instructions for performing processing according to aspects and methodologies disclosed herein.

The computer system 1100 may also include computer components such as a random access memory (RAM) 1106, which may be SRAM, DRAM, SDRAM, or the like. The computer system 1100 may also include read-only memory (ROM) 1108, which may be PROM, EPROM, EEPROM, or the like. RAM 1106 and ROM 1108 hold user and system data and programs, as is known in the art. The computer system 1100 may also include an input/output (I/O) adapter 1110, a communications adapter 1122, a user interface adapter 1124, and a display adapter 1118. The I/O adapter 1110, the user interface adapter 1124, and/or communications adapter 1122 may, in certain aspects and techniques, enable a user to interact with computer system 1100 to input information.

The I/O adapter 1110 preferably connects a storage device(s) 1112, such as one or more of hard drive, compact disc (CD) drive, floppy disk drive, tape drive, etc. to computer system 1100. The storage device(s) may be used when RAM 1106 is insufficient for the memory requirements associated with storing data for operations of embodiments of the present techniques. The data storage of the computer system 1100 may be used for storing information and/or other data used or generated as disclosed herein. The communications adapter 1122 may couple the computer system 1100 to a network (not shown), which may enable information to be input to and/or output from system 1100 via the network (for example, a wide-area network, a local-area network, a wireless network, any combination of the foregoing). User interface adapter 1124 couples user input devices, such as a keyboard 1128, a pointing device 1126, and the like, to computer system 1100. The display adapter 1118 is driven by the CPU 1102 to control, through a display driver 1116, the display on a display device 1120. Information and/or representations of one or more 2D canvases and one or more 3D windows may be displayed, according to disclosed aspects and methodologies.

The architecture of system 1100 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the method may be implemented in machine-readable logic, such that a set of instructions or code that, when executed, performs automated sampling operations from memory. That is, the buoy may be configured to operate in an autonomous mode. As an example, operating in an autonomous manner may include sampling the potential target materials without the interaction of an operator. In such configurations, the buoy may include a control unit, which may be the computer system 1100 as noted in FIG. 11. During the deployment, the buoy may detect targeted materials. The deployment may also include inserting certain equipment (e.g., certain monitoring components) into the buoy for use in sampling operations. As an example, the deployment may include lowering the buoy from the deck of a marine vessel into the body of water or dropping the buoy into the body of water from an airborne vehicle.

The control unit may manage the operations of the communication components, sampling components, measurement components, power components and storage components. The control unit may be configured to adjust the operation of the detection and identification components. That is, the control unit may have the detection and identification components perform the detection operations in a specific sequence. For example, the operations may involve deploying the unmanned vehicle (e.g., balloon) with detection equipment to identify target materials. Then, the target material detection module (e.g., fluorometer and/or wavelength detection components) may be utilized. Further, the control unit may also control the sampling operations. As noted above, the sampling operations may be controlled by the control unit to obtain a certain number of samples, the duration the samples are in contact with the target material and other such operational aspects.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other.

The invention claimed is:

1. A method for identifying and sampling target materials with one or more buoys, comprising:
deploying one or more buoys to a location in a body of water, wherein at least one of the one or more buoys has a buoy monitoring section that includes a measurement component and a sampling component, wherein the sampling component comprises a sampling assembly comprising a plurality of individual sampling containers;
obtaining measurement data associated with the body of water with a measurement component;
determining whether target material is present in the measurement data, wherein the target material comprises one or more of biological, chemical, hydrocarbon and any combination thereof;
obtaining a sample of the target material with the sampling component when the measurement data indicates the presence of the target material; and
storing the obtained sample in one or more of the individual sample containers.

2. The method of claim 1, wherein the at least one of the one or more buoys has a storage component configured to maintain the sample within a specific temperature range.

3. The method of claim 2, wherein the temperature is maintained within the temperature range between about −10° C. and about −100° C.

4. The method of claim 2, wherein the temperature is maintained within the temperature range between about −10° C. and about 10° C.

5. The method of claim 1, wherein the buoy monitoring section further comprises a communication component and wherein deploying the one or more buoys comprises programming the one or more buoys to be able to communicate with the command unit.

6. The method of claim 1, wherein each of the one or more buoys has a floating section that is partially disposed in the body of water and extends out of the body of water, a skirt and ballast section beneath the floating section, and an anchor section that secures the buoy at a relatively fixed location.

7. The method of claim 1, wherein the obtaining measurement data comprises obtaining an indication whether the floating section is in contact with hydrocarbons.

8. The method of claim 1, further comprising performing remote sensing in a survey area to identify the potential location of the target material.

9. The method of claim 1, wherein obtaining the sample of the target material comprises:
contacting sampling material from one of a plurality of sample containers with the target material; and
retrieving the sampling material having adhered target material as the obtained sample into one of the plurality of sample containers.

10. The method of claim 1, wherein obtaining the sample of the target material comprises:
unsealing a sampling vessel to obtain a fluid;
sealing the sampling vessel with the fluid disposed within the sampling vessel;
retrieving the sampling vessel having the fluid disposed within the sampling vessel as the obtained sample into one of a plurality of sample containers.

11. The method of claim 1, wherein obtaining the sample of the target material comprises:
passing a fluid through a sampling conduit to interact with a sampling material;
interrupting the fluid passing through the sampling conduit; and
using the sampling conduit as the sample.

12. The method of claim 1, wherein obtaining the sample of the target material comprises:
passing a fluid through a filter;
passing the fluid through a solid phase extraction module; and
using one or more of the filter and the solid phase extraction module as the sample.

13. The method of claim 1, further comprising determining to obtain the sample based on an indication in the measurement data that the target material is present comprises: pumping a fluid from the body of water through a target measurement device to indicate the presence of the target material; and notifying the sampling component to obtain a sample if the target material is present.

14. The method of claim 1, wherein obtaining the sample of the target material comprises:
acquiring one or more images with an imaging module associated with at least one sampling container; and
retrieving the sampling container as the obtained sample into one of the plurality of sample containers.

15. The method of claim 1, wherein the one or more buoys comprise at least two buoys coupled together with a boom, wherein the boom is configured to direct fluids toward a sample collection location.

16. The method of claim 1, wherein the measurement component comprises a target detection module comprising a mass spectrometer.

17. A buoy monitoring and sampling system comprising:
a buoy having a buoy monitoring section that includes a measurement component and a sampling component;
wherein the measurement component is configured to obtain measurement data associated with the body of water and to identify a target material, wherein the measurement component comprises a target detection module configured to identify target material and notify the sampling component if the target material is present; and
wherein the sampling component is configured to obtain a sample when the measurement component notifies the sampling component of the presence of target material, wherein the sampling component comprises a sampling assembly comprising a plurality of individual sampling containers.

18. The system of claim 17, further comprising a command unit; and
wherein the buoy includes a communication component; wherein the communication component is configured to communicate data with the command unit.

19. The system of claim 17, wherein the buoy includes:
a floating section that is partially disposed in the body of water and extends out of the body of water,
a skirt and ballast section beneath the floating section, wherein the skirt and ballast section is configured to maintain proper buoy orientation relative to the water surface; and
an anchor section that secures the buoy at a relatively fixed location.

20. The system of claim 17, wherein one or more of the plurality of individual sampling containers has a sampling material disposed around a spool within the sampling container.

21. The system of claim 20, wherein one or more of the plurality of individual sampling containers has buoyant weight coupled to the sampling material.

22. The system of claim 21, wherein each of the sampling containers has a guide member disposed between the spool and the buoyant weight.

23. The system of claim 17, wherein the sampling material is TFE-fluorocarbon polymer screening fabric.

24. The system of claim 17, wherein one or more of the plurality of individual sampling containers has a sampling vessel that is configured to unseal the sampling vessel to obtain a fluid; and seal the sampling vessel with the fluid disposed within the sampling vessel.

25. The system of claim 17, wherein one or more of the plurality of individual sampling containers comprises a sampling conduit configured to pass a fluid from the body of water through a sampling material within the sampling conduit.

26. The system of claim 17, wherein one or more of the plurality of individual sampling containers comprises a sampling conduit configured to pass a fluid from the body of water through a sampling material within the sampling conduit.

27. The system of claim 17, wherein the buoy further comprises a storage component configured to maintain the temperature within each of the sampling containers within a specified temperature range.

28. The system of claim 27, wherein the temperature is maintained within the temperature range between about −10° C. and about −100° C.

29. The system of claim 27, wherein the temperature is maintained within the temperature between about −10° C. and about 10° C.

30. The system of claim 17, wherein the target detection module is one of a fluorometer, mass spectrometer, and any combination thereof.

31. The system of claim 17, further comprising an unmanned vehicle having a propulsion component, a communication component, and a sample collection component, wherein the propulsion component is configured to maneuver the unmanned vehicle, the sample collection component is configured to obtain one or more samples from the buoy, and the communication component is configured to communicate with the buoy.

32. The system of claim 17, wherein the target detection module comprises a mass spectrometer.

* * * * *